(12) United States Patent
Flickinger et al.

(10) Patent No.: US 11,728,339 B2
(45) Date of Patent: Aug. 15, 2023

(54) SPINAL FIXATION SYSTEMS AND METHODS

(71) Applicant: Meditech Spine, LLC, Atlanta, GA (US)

(72) Inventors: Eric Flickinger, Atlanta, GA (US); Robert Bruce Dunaway, Akron, OH (US)

(73) Assignee: Meditech Spine, LLC, Atlanta, GA (US)

( * ) Notice: Subject to any disclaimer, the term of this patent is extended or adjusted under 35 U.S.C. 154(b) by 0 days.

(21) Appl. No.: 17/026,791

(22) Filed: Sep. 21, 2020

(65) Prior Publication Data

US 2021/0085482 A1 Mar. 25, 2021
US 2022/0000635 A9 Jan. 6, 2022

Related U.S. Application Data

(60) Provisional application No. 62/905,270, filed on Sep. 24, 2019.

(51) Int. Cl.
*A61F 2/44* (2006.01)
*H01L 27/088* (2006.01)
*A61B 17/70* (2006.01)
*A61F 2/46* (2006.01)

(52) U.S. Cl.
CPC ...... *H01L 27/0886* (2013.01); *A61B 17/7059* (2013.01); *A61F 2/4455* (2013.01); *A61F 2/4684* (2013.01)

(58) Field of Classification Search
CPC ................ A61F 2/44–447; A61B 17/7059
See application file for complete search history.

(56) References Cited

U.S. PATENT DOCUMENTS

| 6,565,571 | B1 * | 5/2003 | Jackowski | A61B 17/1728 606/286 |
| 7,172,627 | B2 * | 2/2007 | Fiere | A61F 2/4611 623/17.11 |
| 9,730,804 | B2 * | 8/2017 | Cowan, Jr. | A61F 2/447 |
| 10,603,187 | B2 * | 3/2020 | Laubert | A61F 2/30942 |
| 10,849,763 | B2 * | 12/2020 | Lauf | A61B 17/70 |
| 2002/0147450 | A1 * | 10/2002 | LeHuec | A61B 17/8042 606/86 B |
| 2005/0085913 | A1 * | 4/2005 | Fraser | A61B 17/7059 623/17.11 |
| 2008/0051890 | A1 * | 2/2008 | Waugh | A61F 2/442 623/17.11 |
| 2008/0294262 | A1 * | 11/2008 | Levieux | A61F 2/4611 623/17.16 |
| 2014/0066997 | A1 * | 3/2014 | Humphreys | A61B 17/7059 606/294 |
| 2016/0095714 | A1 * | 4/2016 | Spangler | A61L 31/06 623/17.16 |
| 2016/0128746 | A1 * | 5/2016 | Dunaway | A61B 17/8042 606/246 |
| 2018/0289495 | A1 * | 10/2018 | Gray | A61B 17/7059 |
| 2018/0303629 | A1 * | 10/2018 | Lauf | A61B 17/8605 |

* cited by examiner

*Primary Examiner* — Nicholas J Plionis

(57) ABSTRACT

A spinal fixation system includes an interbody and a plate. The interbody defines at least one locking aperture. The plate includes a front surface, a back surface, and at least one locking projection extending from the back surface. The at least one locking projection is removably engaged with the at least one locking aperture such that the plate is removably coupled to the interbody.

16 Claims, 17 Drawing Sheets

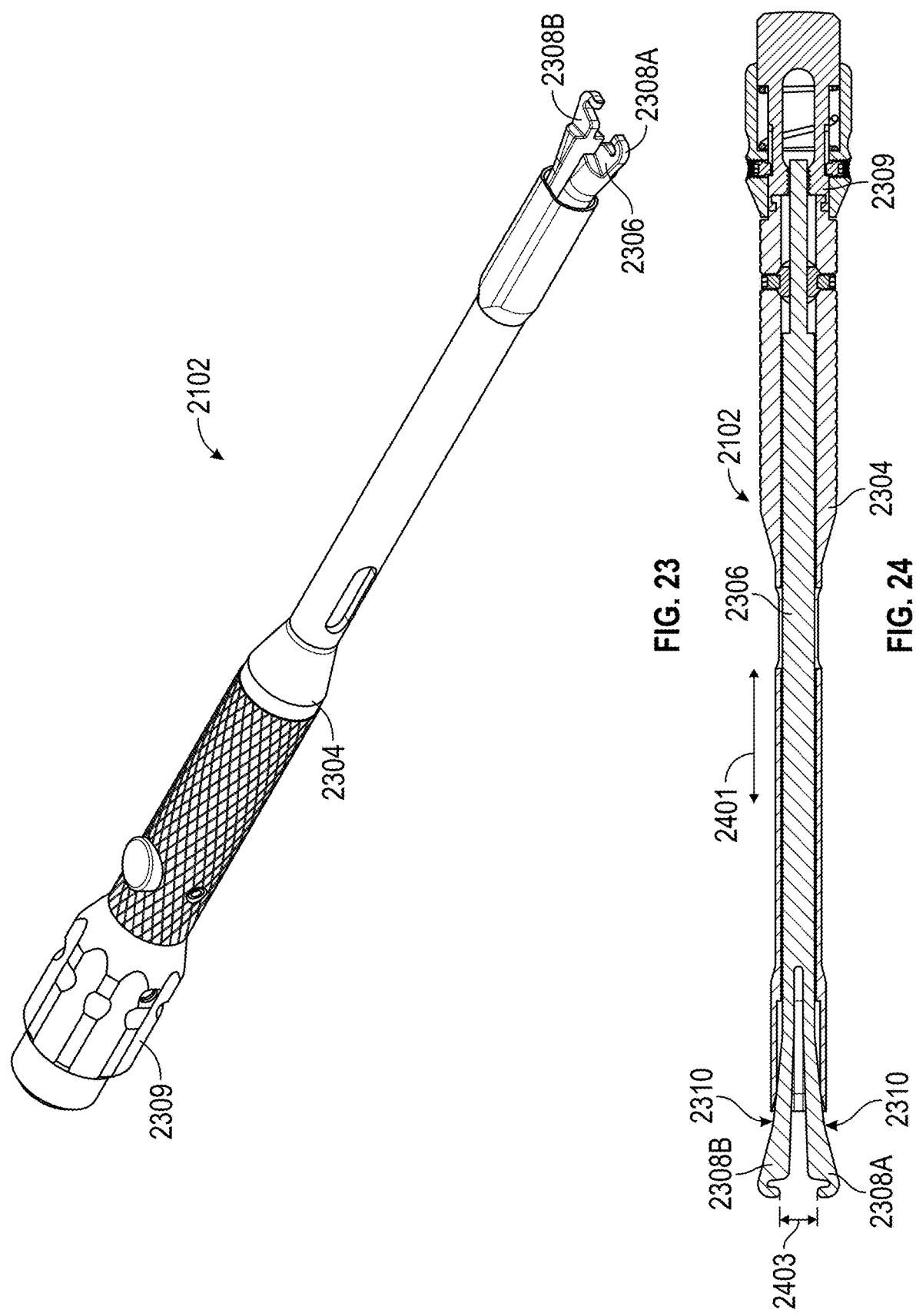

SPINAL FIXATION SYSTEMS AND METHODS

REFERENCE TO RELATED APPLICATION

This application claims the benefit of U.S. Provisional Patent Application No. 62/905,270, filed on Sep. 24, 2019, and entitled SPINAL FIXATION SYSTEMS AND METHODS, the content of which is hereby incorporated by reference in its entirety

FIELD OF THE INVENTION

The field of the invention relates to devices, systems, and processes for spinal surgeries, and, in particular, to spinal fixation systems.

BACKGROUND

Spinal fusion is a surgical technique used to join two or more vertebrae for the correction of various conditions such as back pain caused by degenerative conditions, misalignment, scoliosis, injury causing misalignment, or abnormal intervertebral motion. Spinal fusion may be indicated for the cervical region or, (more rarely), the thoracic or lumbar regions.

Spinal fusion, and particularly intervertebral (or interbody) fusion, is accomplished by immobilizing vertebrae relative to one another with one or more surgical implants, removing a portion of material between the vertebrae, and providing graft material between the vertebrae. The material removed typically includes the intervertebral disk, but may often include part(s) of one or both of the adjacent vertebrae. Graft material typically includes supplementary bone material, which may be obtained from the recipient, a donor, a synthetic substitute, or any suitable combination of the above.

Successful fusion requires that the relative orientation of the fused vertebrae be maintained, as well as the spacing between them. Although the vertebrae may be fixed by mechanical implants, such as rods, plates, or cages connected to the vertebrae by screws, or by exterior support in the form of orthotic bracing, these approaches are limited and are susceptible to various problems such as the backing out of bone screws, misalignment, etc.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various embodiments of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

According to certain examples, a spinal fixation system includes an interbody and a plate. The interbody defines a locking aperture, and the plate includes a front surface, a back surface, a locking projection extending from the back surface, and at least one bone screw aperture extending from the front surface to the back surface. The locking projection is removably engaged with the locking aperture such that the plate is removably coupled to the interbody.

According to various examples, a spinal fixation system includes an interbody that defines a locking aperture. The spinal fixation system also includes a plate that includes a locking projection and defines a locking cam aperture. The spinal fixation system includes a locking cam that has a stem and a tab. The locking projection is removably engaged with the locking aperture, and the stem of the locking cam is at least partially positioned within the locking cam aperture.

According to some examples, a plate for a spinal fixation system includes a body having a front surface and a back surface. The plate also includes a locking projection extending outwardly from the back surface of the body. The plate further includes a locking cam aperture extending through the body from the front surface to the back surface. The plate additionally includes a bone screw aperture extending through the body from the front surface to the back surface.

Various implementations described in the present disclosure can include additional systems, methods, features, and advantages, which cannot necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures can be designated by matching reference characters for the sake of consistency and clarity.

FIG. 23 is a perspective view of the tool of FIG. 21.

FIG. 24 is a sectional view of the tool of FIG. 21.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described. Directional references such as "up," "down," "top," "bottom," "left," "right," "front," and "back," among others, are intended to refer to the orientation as illustrated and described in the figure (or figures) to which the components and directions are referencing.

Embodiments of the present disclosure are directed towards spinal fixation systems and associated methods, systems, devices, and apparatuses. The disclosed spinal fixation systems are described in but a few exemplary aspects among many.

Figure 6:
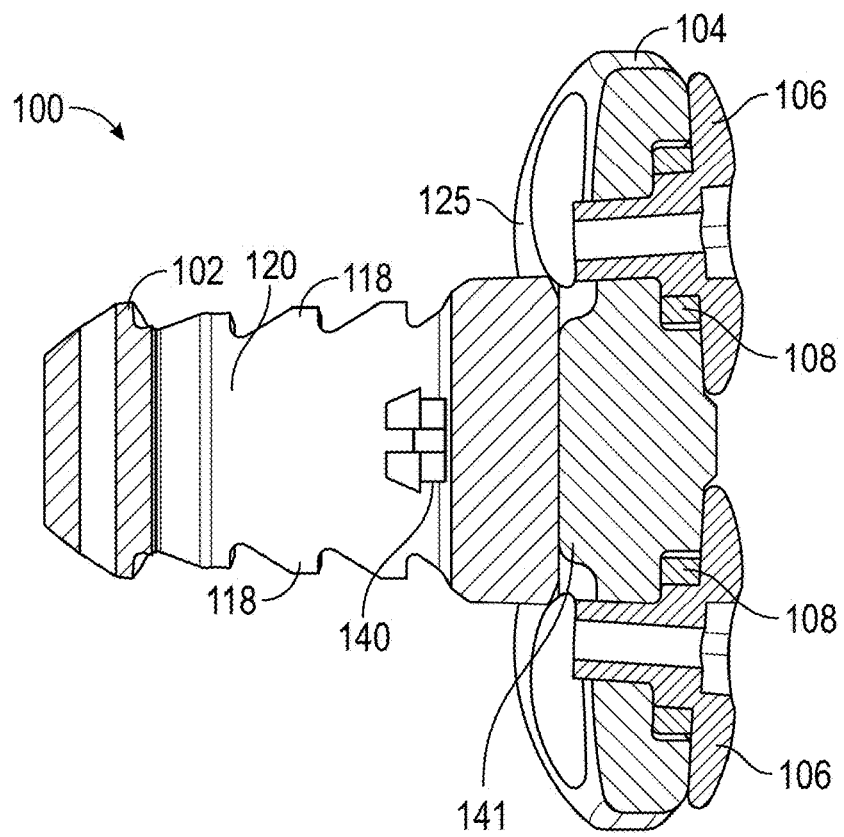
FIG. 6 is a sectional view of the spinal fixation system of FIG. 1 taken along line 6-6 in FIG. 5.
Figure 7:
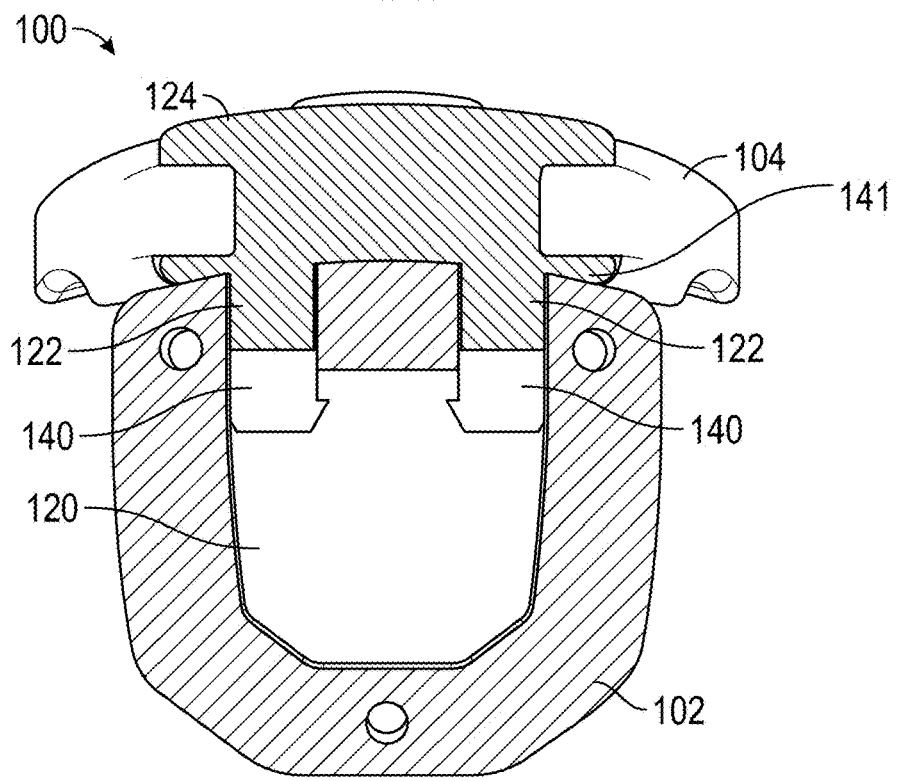
FIG. 7 is a sectional view of the spinal fixation system of FIG. 1 taken along line 7-7 in FIG. 4.

FIGS. 1-20 illustrate an example of a spinal fixation system 100 that includes an interbody 102 and a plate 104. As discussed in detail below, the spinal fixation system 100 may also include a locking cam 106 and a locking collar 108 (FIG. 6). The components of the spinal fixation system 100 may be constructed from various suitable biocompatible materials such that the implant can be provided within a patient's body. As one example, the interbody 102 may be constructed from polyetheretherketone ("PEEK"), hydroxyapatite polyetheretherketone ("HA PEEK"), or other suitable materials, and the plate 104 may be constructed from a metal, such as titanium or others. In some examples, one or more components of the spinal fixation system 100 may be coated, surface-altered, and/or impregnated with various materials using various known techniques.

The interbody 102 includes a front surface 110, a back surface 112, an upper surface 114, and a lower surface 116. The shape and profile of the interbody 102 illustrated in FIGS. 1-20 should not be considered limiting on the current disclosure, as in other examples, the interbody 102 may have various suitable shapes and profiles as desired. In some cases, gripping portions 118 may be provided on the upper surface 114 and/or the lower surface 116 to engage the vertebrae of the patient. In various examples, the interbody 102 defines a central opening 120 that is configured for receiving graft material that helps the interbody 102 fuse with the vertebrae of the patient when the spinal fixation system 100 is positioned within an intervertebral disc space of the patient's body. The shape of the central opening 120 should not be considered limiting on the current disclosure. Various other openings or apertures may be provided on the interbody 102 as desired.

Figure 8:
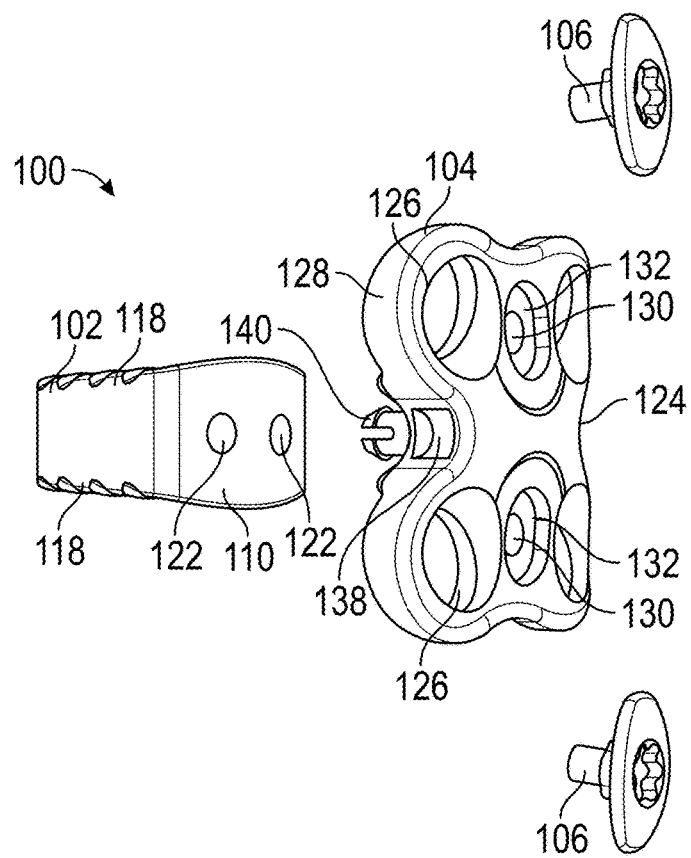
FIG. 8 is an exploded assembly view of the spinal fixation system of FIG. 1.
Figure 9:
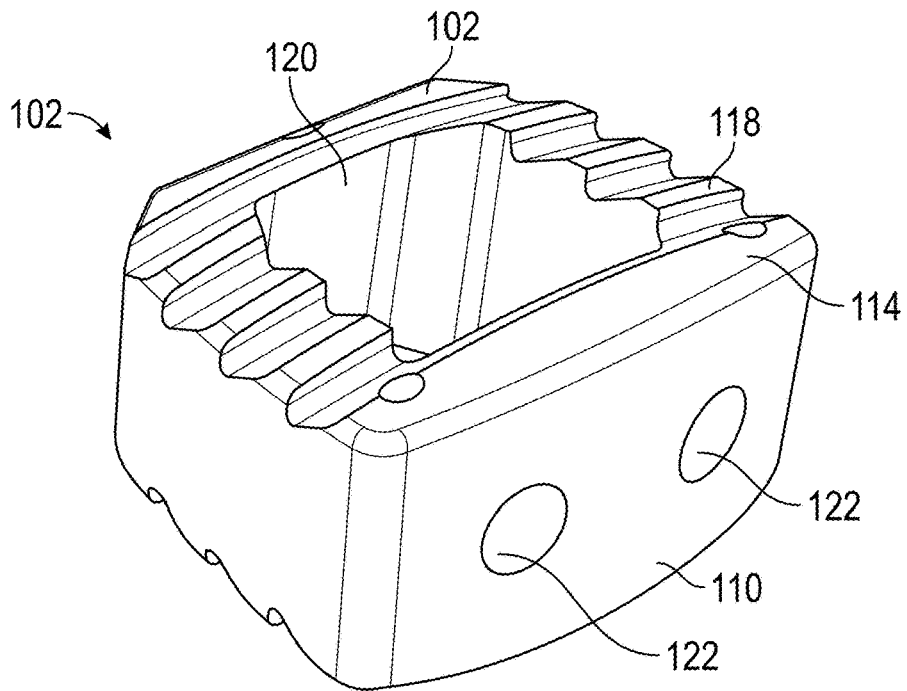
FIG. 9 is a perspective view of an interbody of the spinal fixation system of FIG. 1.

In various examples, the interbody 102 defines one or more locking apertures 122 (see FIG. 8, for example). In various aspects, each locking aperture 122 extends from the front surface 110 to the central opening 120. In some examples, a central axis of one of the locking apertures 122 is substantially parallel with a central axis of another locking aperture 122, although it need not be in other examples. While two locking apertures 122 are shown, in other examples, the interbody 102 may include any number of locking apertures as desired such as one locking aperture, three locking apertures, etc. As discussed in detail below, the locking apertures 122 may receive locking projections of the plate 104 such that the plate 104 is selectively coupled to the interbody 102.

The plate 104 includes a front surface 124, a back surface 125, and a perimeter surface 128 between the front surface 124 and the back surface 125. When the plate 104 is assembled with the interbody 102, the back surface 125 of the plate 104 may be positioned adjacent to the front surface 110 of the interbody 102. In certain examples, a shape or profile of the back surface 125 is complimentary to a shape or profile of the front surface 110, although it need not be in other examples. In some non-limiting examples, the front surface 124 and the back surface 125 may have a non-linear curvature in at least one direction, although in other examples, the front surface 124 and/or the back surface 125 may have various suitable profiles as desired.

The plate 104 defines one or more bone screw apertures 126 for receiving bone screws (not illustrated) that engage the vertebrae of the patient and secure the spinal fixation system 100 within the patient's body. In the example of FIGS. 1-20, the plate 104 includes four bone screw apertures 126, although in other examples, any number of bone screw apertures may be utilized. Each bone screw aperture 126 extends from the front surface 124 to the back surface 125. In some examples, the bone screw apertures 126 may extend through the plate 104 at an oblique angle relative to a plane of the front surface 124 and/or the back surface 125, although they need not in other examples. In certain cases, a central axis of one of the bone screw apertures 126 may be non-parallel to a central axis of another one of the bone screw apertures 126.

In various examples, the plate 104 defines one or more locking cam apertures 130. The number of locking cam apertures 130 should not be considered limiting on the current disclosure. In various examples, the number of locking cam apertures 130 corresponds with the number of locking cams 106. In the example of FIGS. 1-20, the plate 104 includes two locking cam apertures 130. Each locking cam aperture 130 extends from the front surface 124 to the back surface 125 of the plate 104. When the spinal fixation system 100 is assembled, a portion of a locking cam 106 may be positioned within each locking cam aperture 130 such that the locking cam 106 is selectively movable between an unlocked position and a locked position. In the unlocked position (best illustrated in FIGS. 1 and 2), the locking cam 106 may allow for the positioning of bone screws in the bone screw apertures 126. In the locked position, a portion of the locking cam 106 overlaps a portion of the bone screw aperture 126 and thus bone screws within the bone screw aperture 126 to prevent the bone screws from backing out of the bone screw apertures 126.

Figure 10:
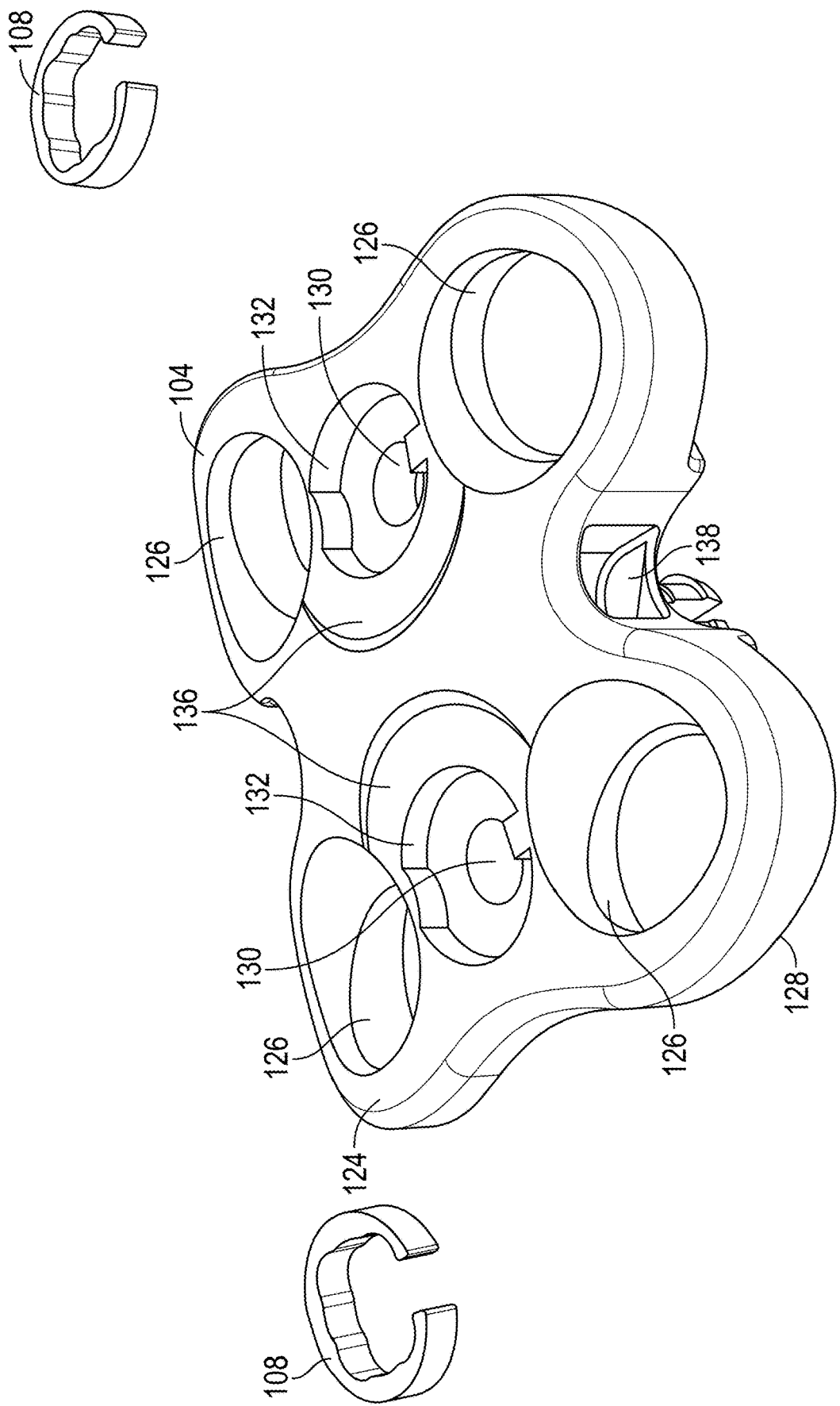
FIG. 10 is an exploded assembly view of a plate and locking collars of the spinal fixation system of FIG. 1.
Figure 11:
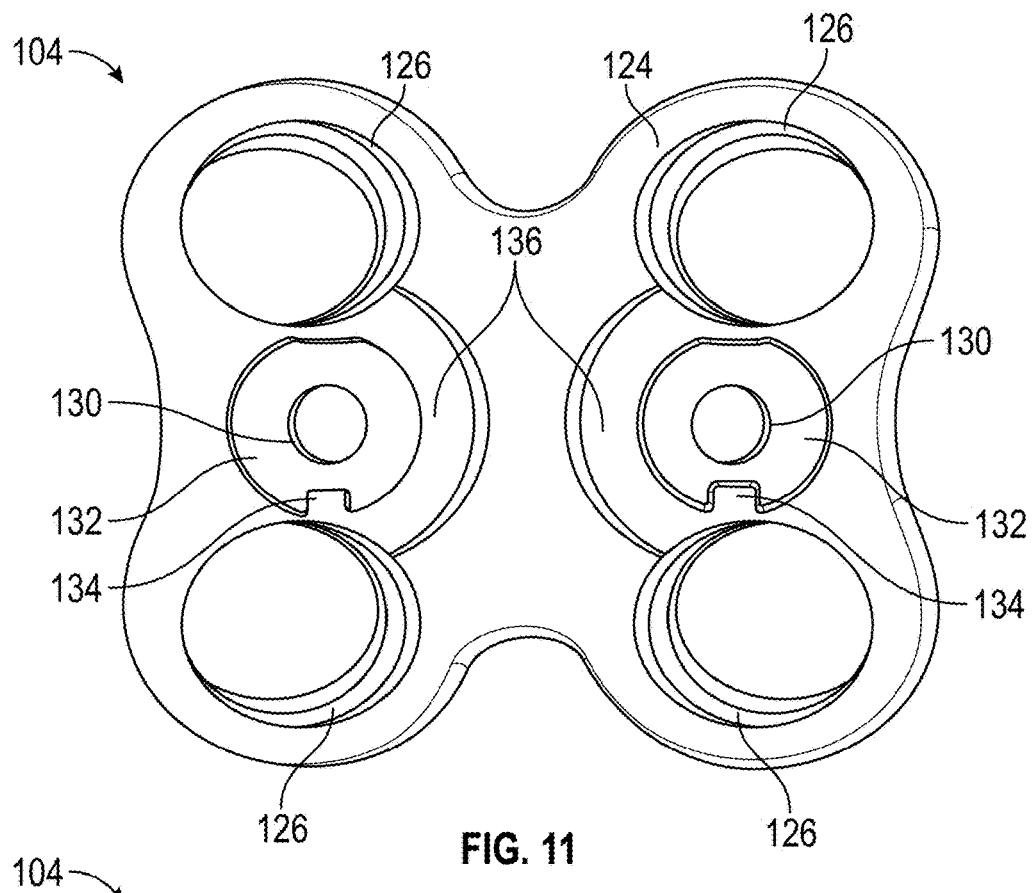
FIG. 11 is a front view of the plate of the spinal fixation system of FIG. 1.
Figure 12:
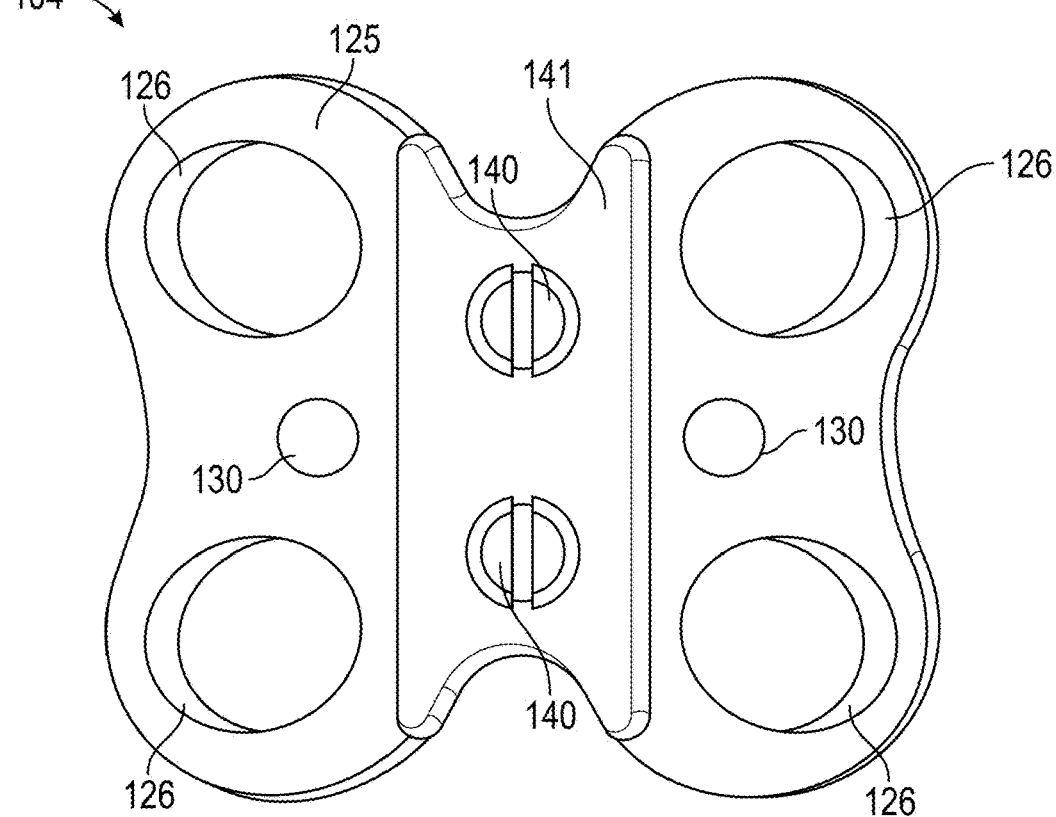
FIG. 12 is a back view of the plate of the spinal fixation system of FIG. 1.

As best illustrated in FIGS. 10 and 11, in various examples, the plate 104 defines a locking collar recess 132 that selectively receives a locking collar 108 when assembled. In some cases, the locking collar recess 132 includes one or more alignment ribs 134 (FIG. 11), which may aid in the positioning and retention of the locking collar 108 within a particular locking collar recess 132. As described in detail below, the locking collar 108 may aid in the positioning and retention of the locking cam 106 on the plate 104. In various cases, each locking cam aperture 130 extends through a corresponding locking collar recess 132.

In some aspects, the plate 104 includes a locking cam recess 136 that at least partially surrounds a corresponding locking cam aperture 130. The locking cam recess 136 may facilitate movement of the locking cam 106 within a particular locking cam recess 136 by minimizing interference between the locking cam 106 and the plate 104 as the locking cam 106 is rotated between the locked and unlocked positions.

As best illustrated in FIGS. 1, 4, 8, 10, and 14, in some cases, the perimeter surface 128 defines one or more tool pockets 138 that selectively receive a portion of an implanting tool during installation of the spinal fixation system 100. Each tool pocket 138 includes a side pocket surface 141 and a bottom pocket surface 139 that is recessed into the plate relative to the perimeter surface 128. In the example of FIGS. 1-20, the perimeter surface 128 includes two tool pockets 138, although any number of tool pockets may be utilized as desired.

Figure 13:
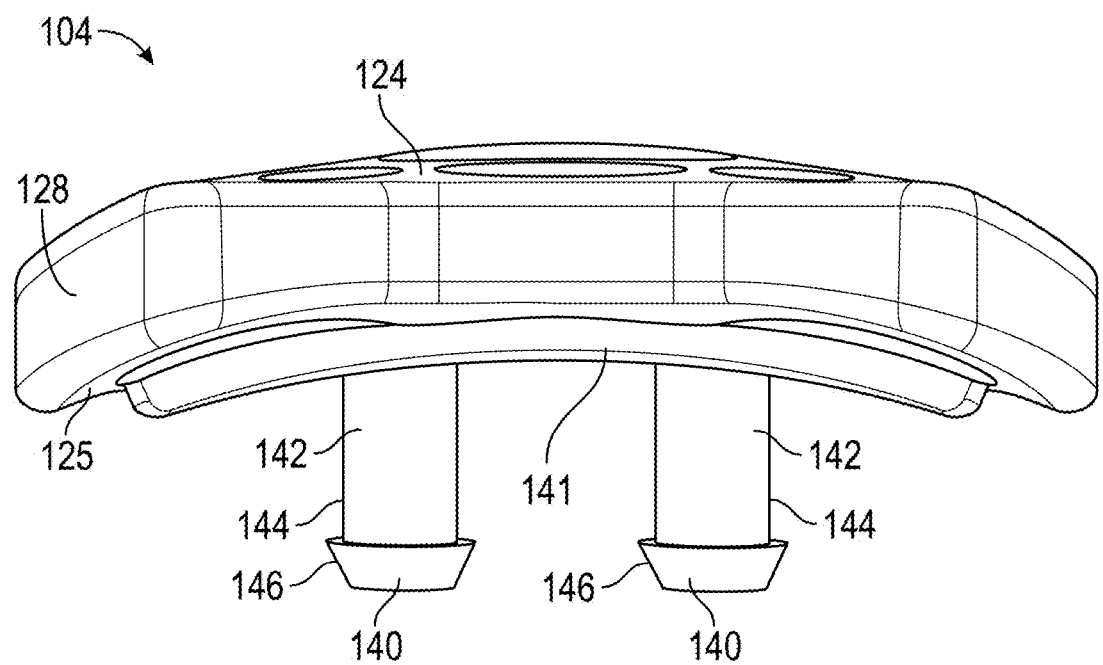
FIG. 13 is a side view of the plate of the spinal fixation system of FIG. 1.
Figure 14:
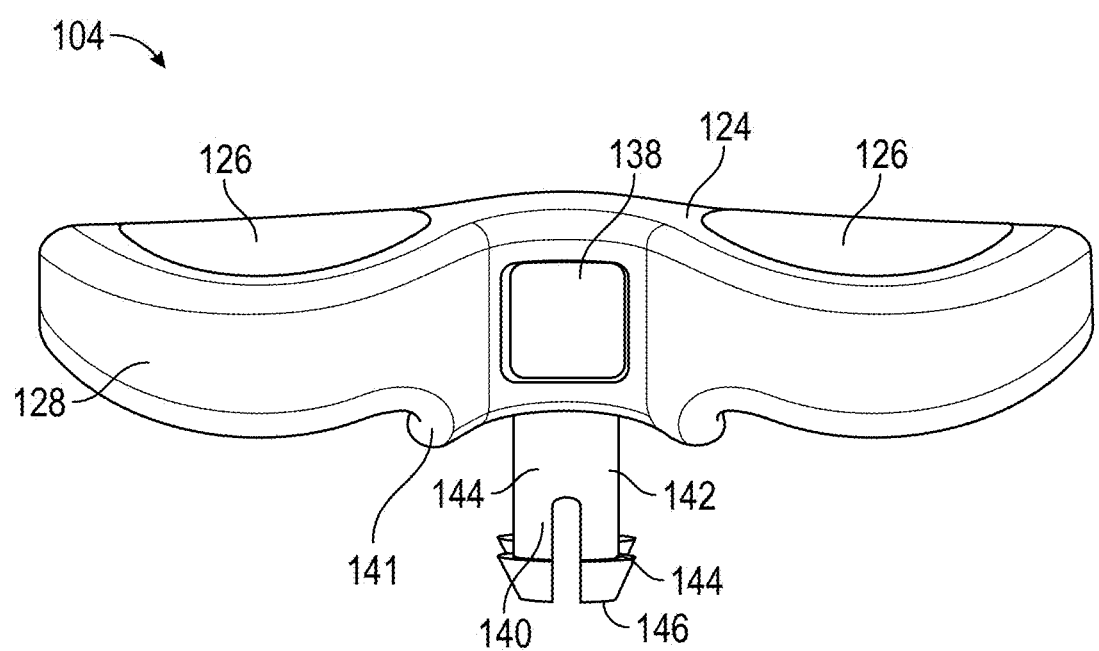
FIG. 14 is another side view of the plate of the spinal fixation system of FIG. 1.

In various examples, the back surface 125 of the plate 104 includes one or more locking projections 140 that are insertable into the locking apertures 122 of the interbody 102 to selectively secure the plate 104 relative to the interbody 102. In the example of FIGS. 1-20, the plate 104 includes two locking projections 140, although in other examples, any desired number of locking projections may be utilized. As shown in FIGS. 13-14, each locking projection 140 includes a stem portion 142 and locking ribs 146. The stem portion 142 is insertable into the corresponding locking aperture 122, and the locking ribs 146 selectively engage the interbody 102. In various examples, the locking ribs 146 selectively engage the interbody 102 within the central opening 120, although they need not in other examples. Optionally, the stem portion 142 includes one or more flex members 144 that bias the locking ribs 146 outwardly such that the locking ribs 146 engage the interbody 102 and the interbody 102 and plate 104 are retained together. A ridge 141 may extend outwards from the back surface 125 as illustrated in FIGS. 5, 6, 12-14, 27, and 28, for example. The locking projections 140 may be on the ridge 141 and extend outwards from the ridge 141. The ridge 141 may contact the interbody 102 when the plate 104 is assembled with the interbody 104 and space the back surface 125 apart from the front surface 110 of the interbody 104 (see, e.g., FIGS. 6 and 7).

Figure 15:
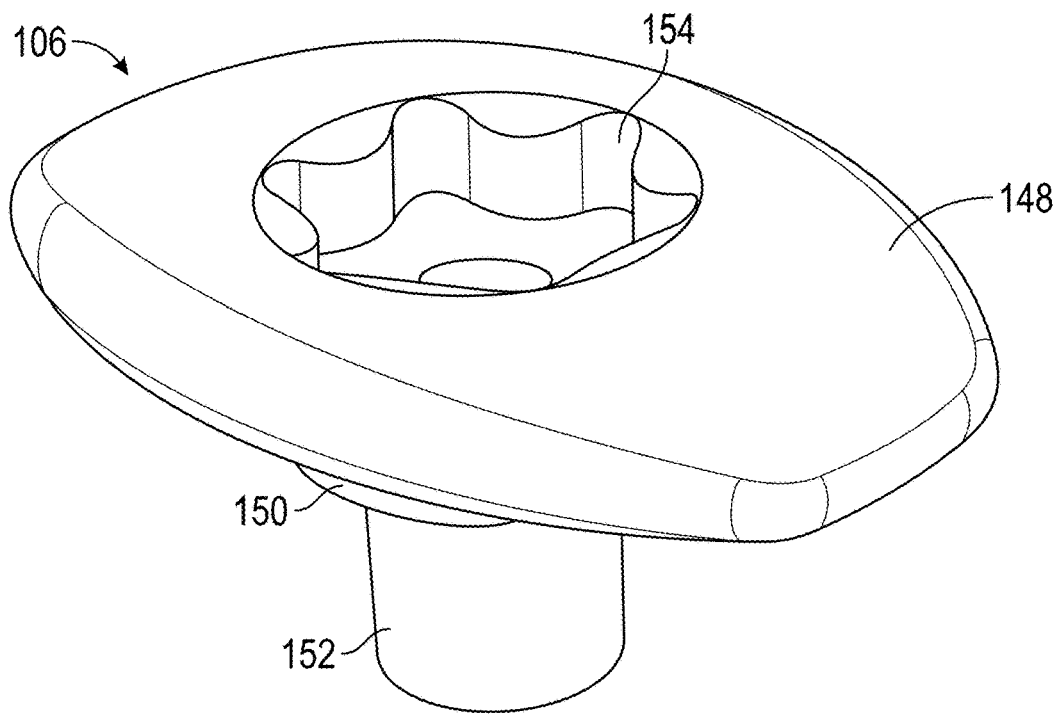
FIG. 15 is a perspective view of a locking cam of the spinal fixation system of FIG. 1.
Figure 16:
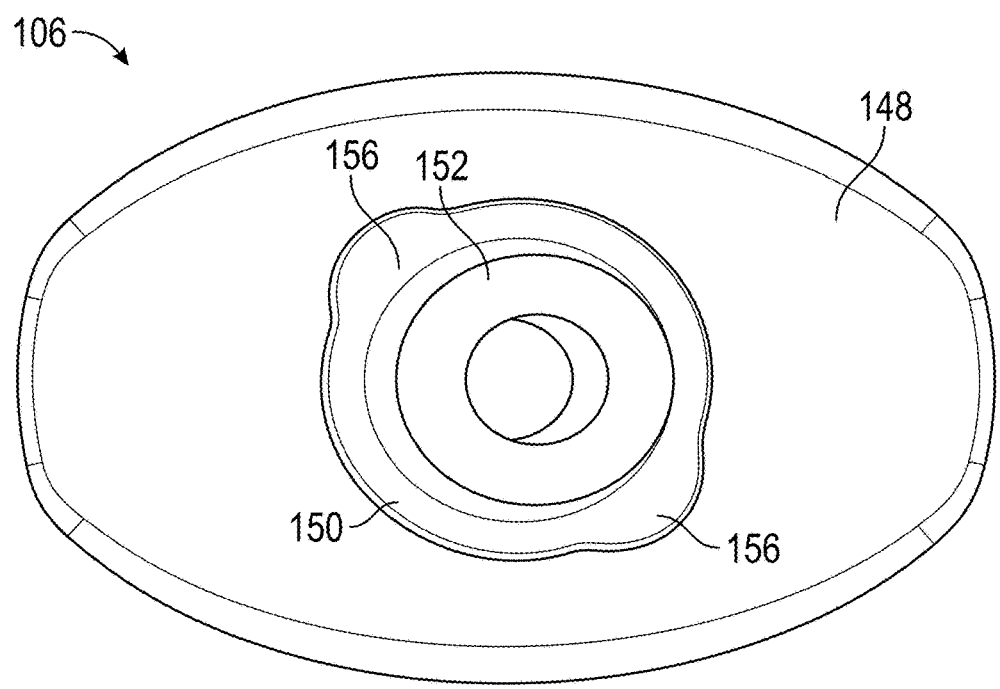
FIG. 16 is a bottom view of the locking cam of the spinal fixation system of FIG. 1.

As best illustrated in FIGS. 15 and 16, each locking cam 106 includes a tab portion 148, a collar 150, and a stem portion 152. In various examples, the locking cam 106 defines a tool recess 154 in the tab portion 148 that can receive a tool that rotates the locking cam 106 between the locked and unlocked positions. The collar 150 is positionable within the locking cam recess 136 of the plate 104 and may include one or more collar ribs 156 that selectively engages the locking collar 108 within the locking cam recess 136. Engagement of the collar ribs 156 within the locking cam recess 136 may selectively maintain the locking cam 106 in the unlocked configuration or the locked configuration. The stem portion 152 of each locking cam 106 is insertable into a corresponding one of the locking cam apertures 130 of the plate 104. Optionally, the stem portion 152 includes one or more flex members and/or locking ribs similar those of the locking projections 140, although it need not in other examples.

Figure 1:
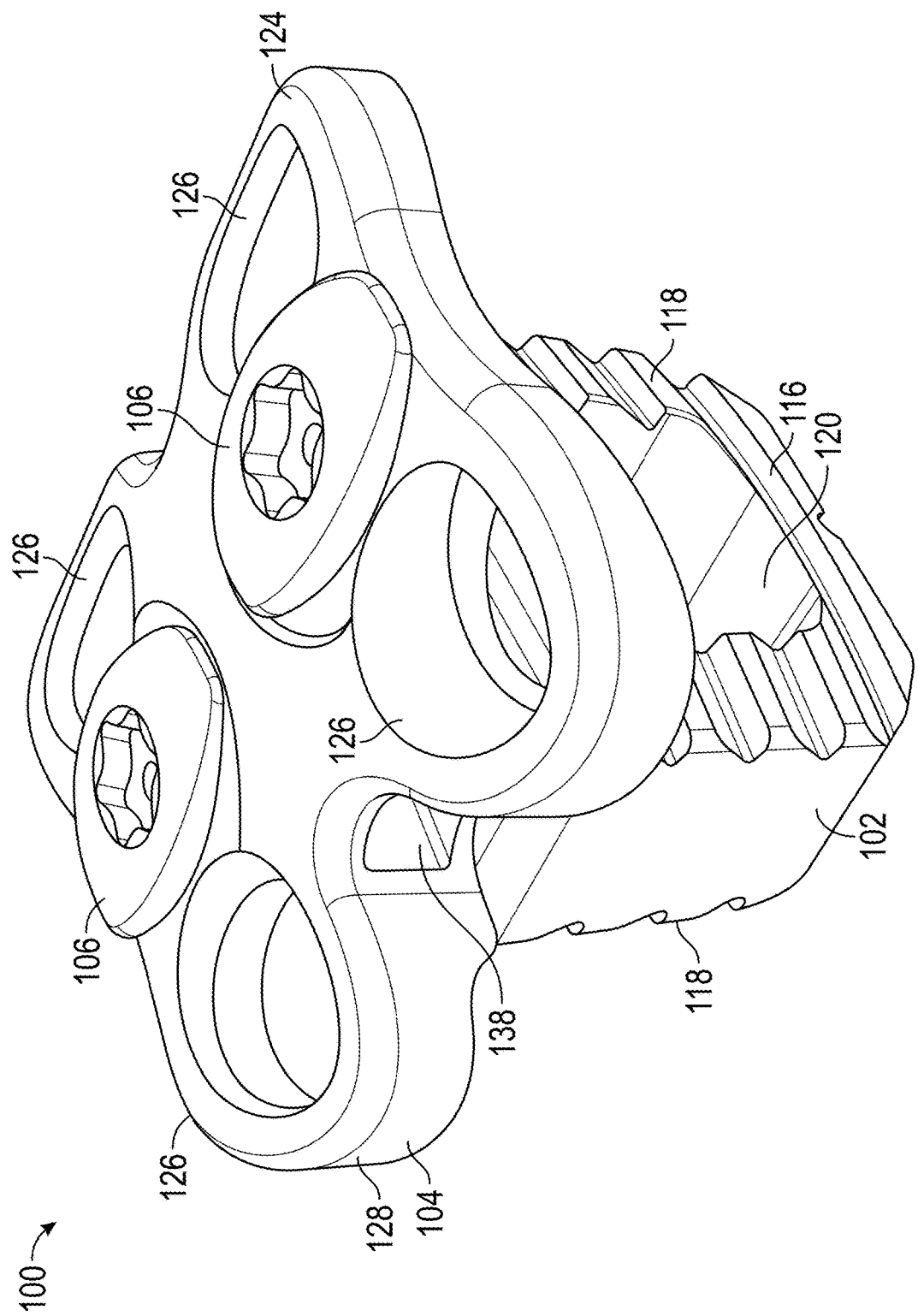
FIG. 1 is a perspective view of a spinal fixation system according to aspects of the current disclosure.
Figure 2:
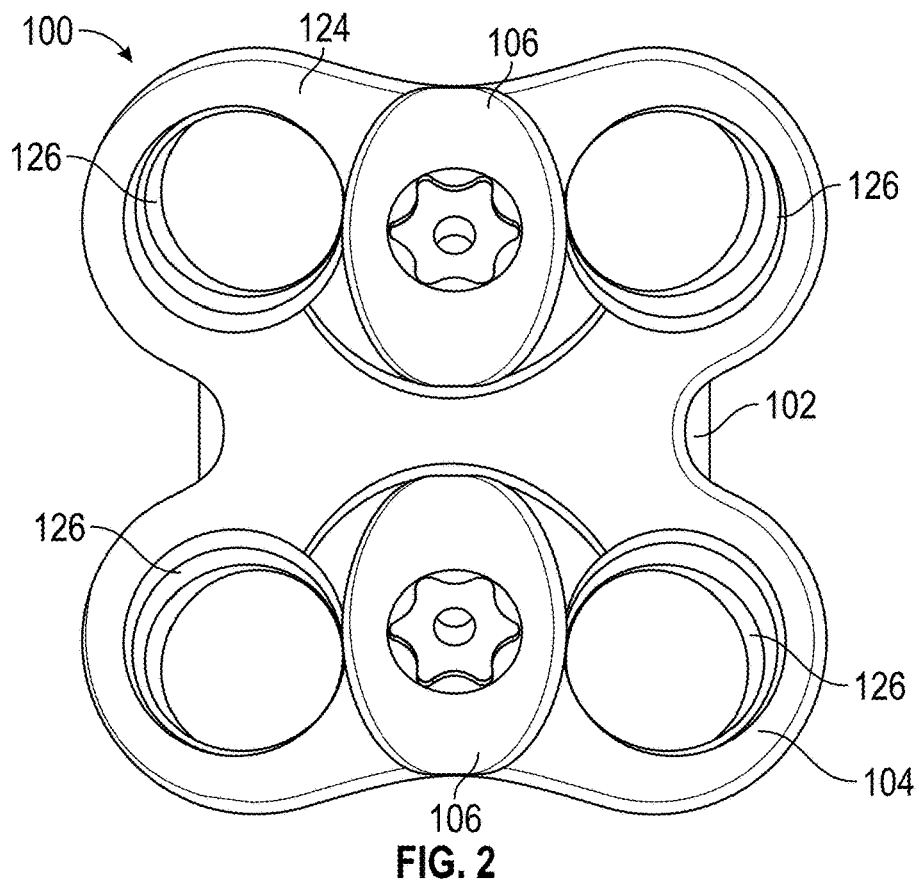
FIG. 2 is a front view of the spinal fixation system of FIG. 1.
Figure 3:
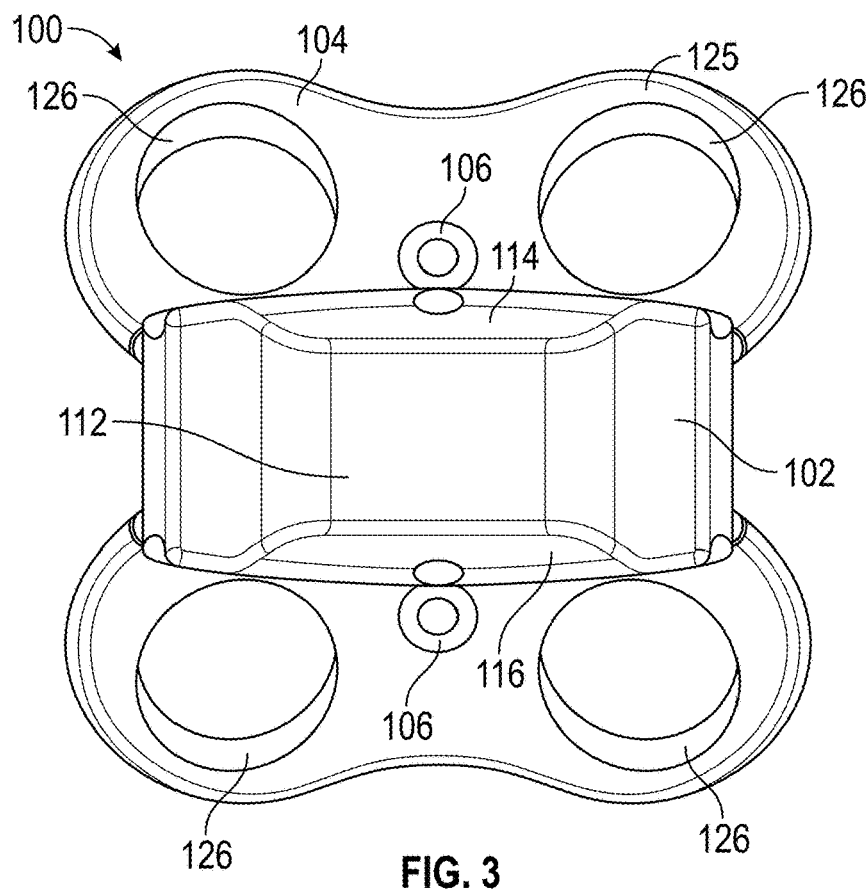
FIG. 3 is a back view of the spinal fixation system of FIG. 1.
Figure 4:
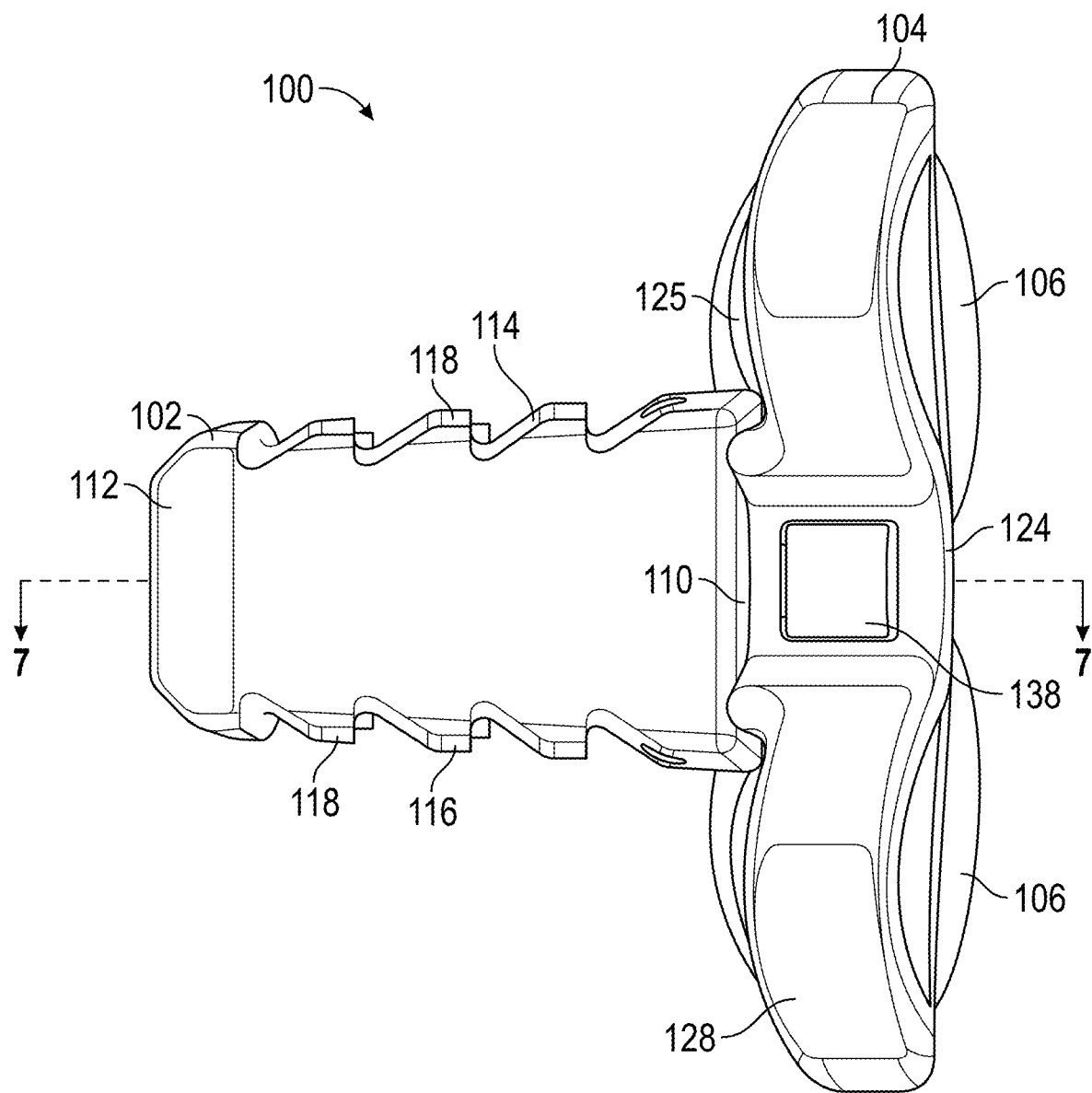
FIG. 4 is a side view of the spinal fixation system of FIG. 1.
Figure 5:
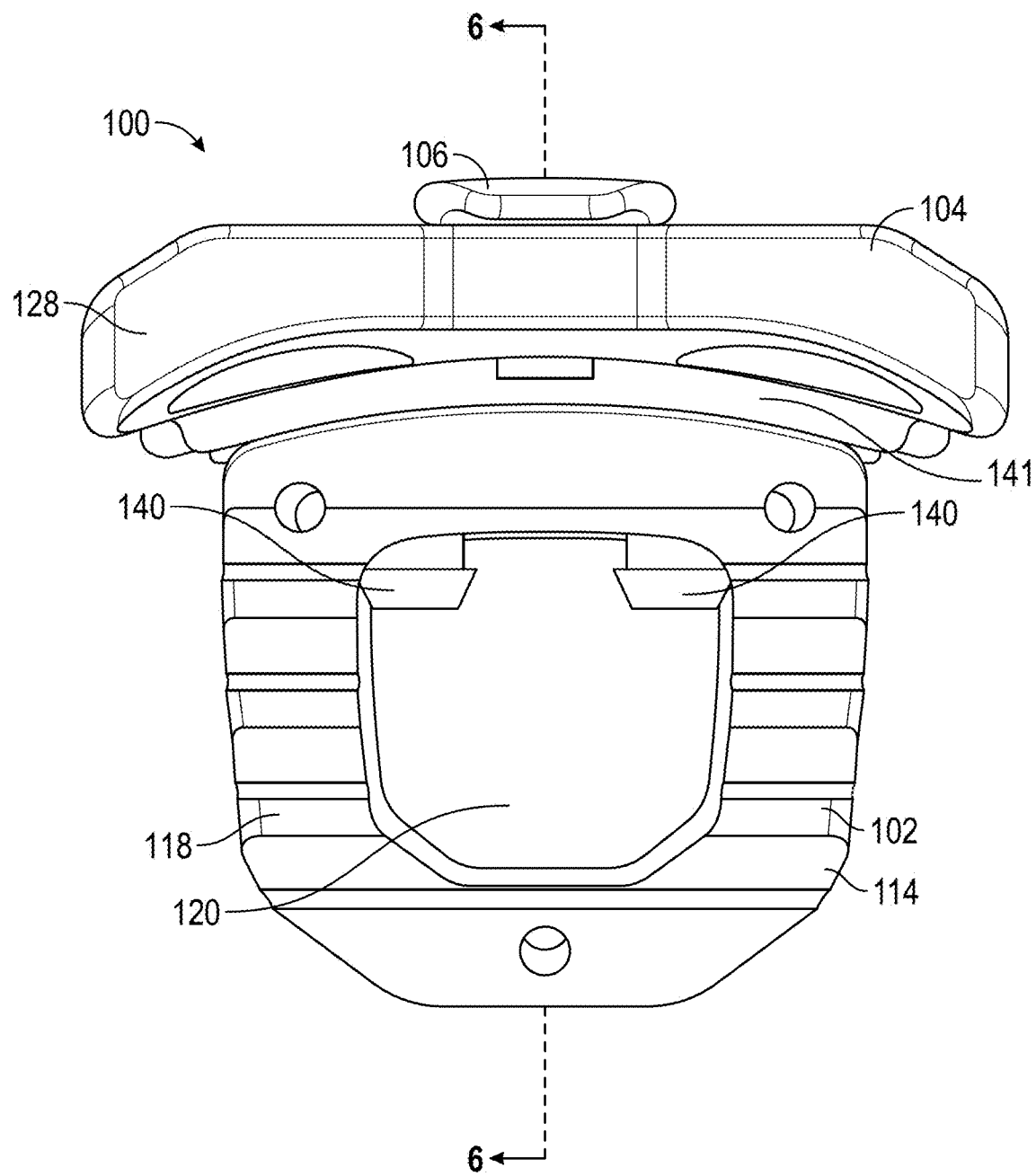
FIG. 5 is a top view of the spinal fixation system of FIG. 1.

In certain aspects, the locking cam 106 is rotatable while the collar 150 is within the locking cam recess 136 such that the locking cam 106 can rotate between the locked configuration (where the tab portions 148 partially overlap the bone screw apertures 126) and the unlocked configuration (where the tab portions 148 do not overlap the bone screw apertures 126). As mentioned, FIGS. 1 and 2 illustrate the locking cams 106 in the unlocked configuration.

Figure 17:
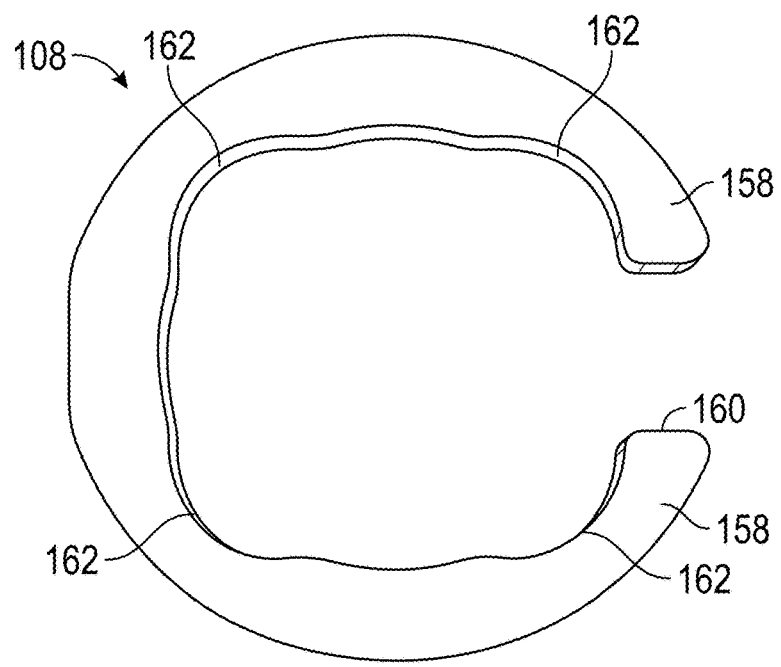
FIG. 17 is a top view of a locking collar of the spinal fixation system of FIG. 1.
Figure 18:
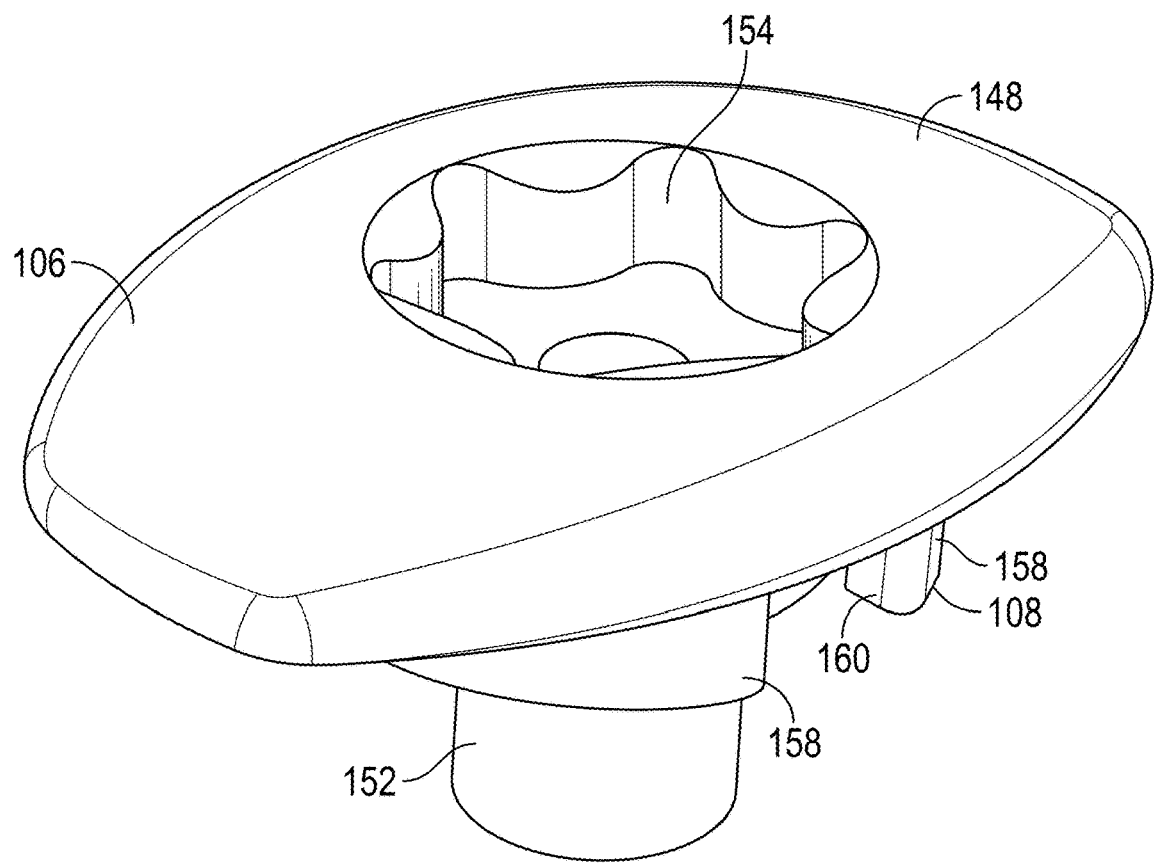
FIG. 18 is a perspective view of the locking collar on the locking cam.
Figure 19:
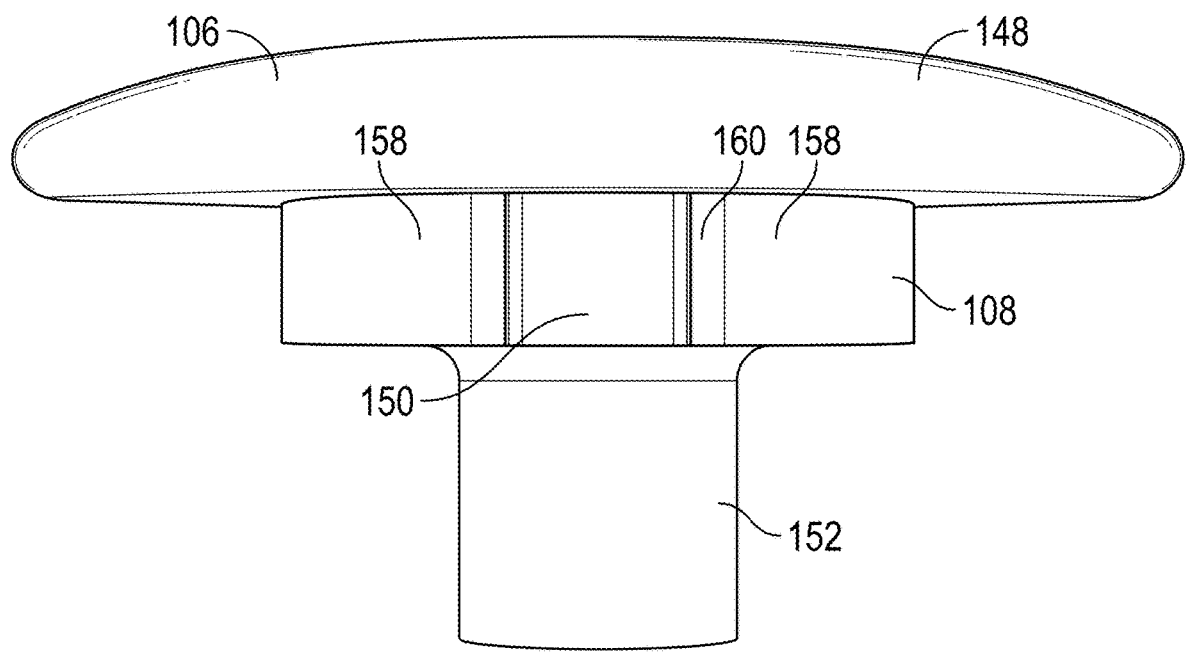
FIG. 19 is a side view of the locking collar on the locking cam.
Figure 20:
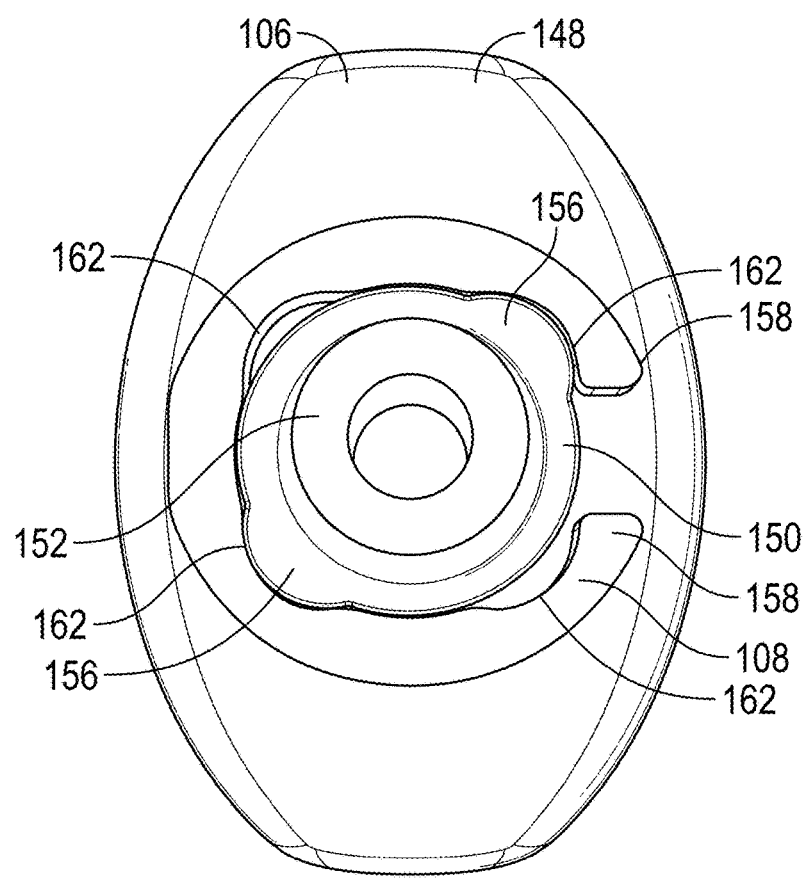
FIG. 20 is a bottom view of the locking collar on the locking cam.

As best illustrated in FIG. 17, each locking collar 108 includes locking arms 158 and/or locking notches 160 that engage with the alignment ribs 134 of the plate 104 such that a position and orientation of the locking collar 108 relative to the plate 104 can be maintained. In some cases, each locking collar 108 also defines cam-locking notches 162 that selectively engage the collar ribs 156 of the corresponding locking cam 106 to maintain the locking cam 106 in the unlocked configuration or the locked configuration. In some cases, the locking collars 108 may be integrally or monolithically formed with the plate 104 as a unitary component, but in other examples, the locking collars 108 are separate components that are assembled with the plate 104.

Figure 21:
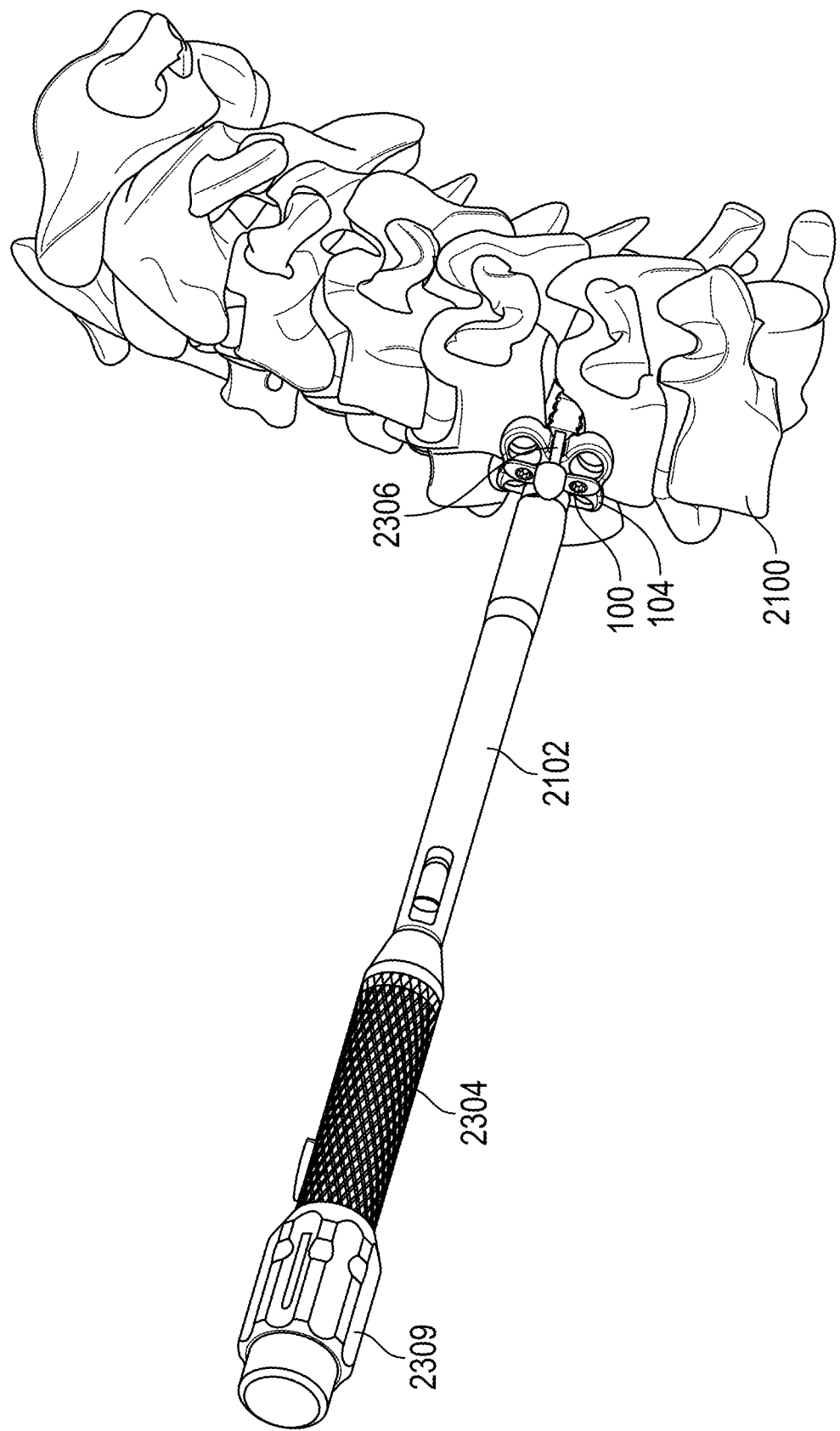
FIG. 21 illustrates a view of the spinal fixation system of FIG. 1 being implanted in a spine with a tool according to aspects of the current disclosure.
Figure 22:
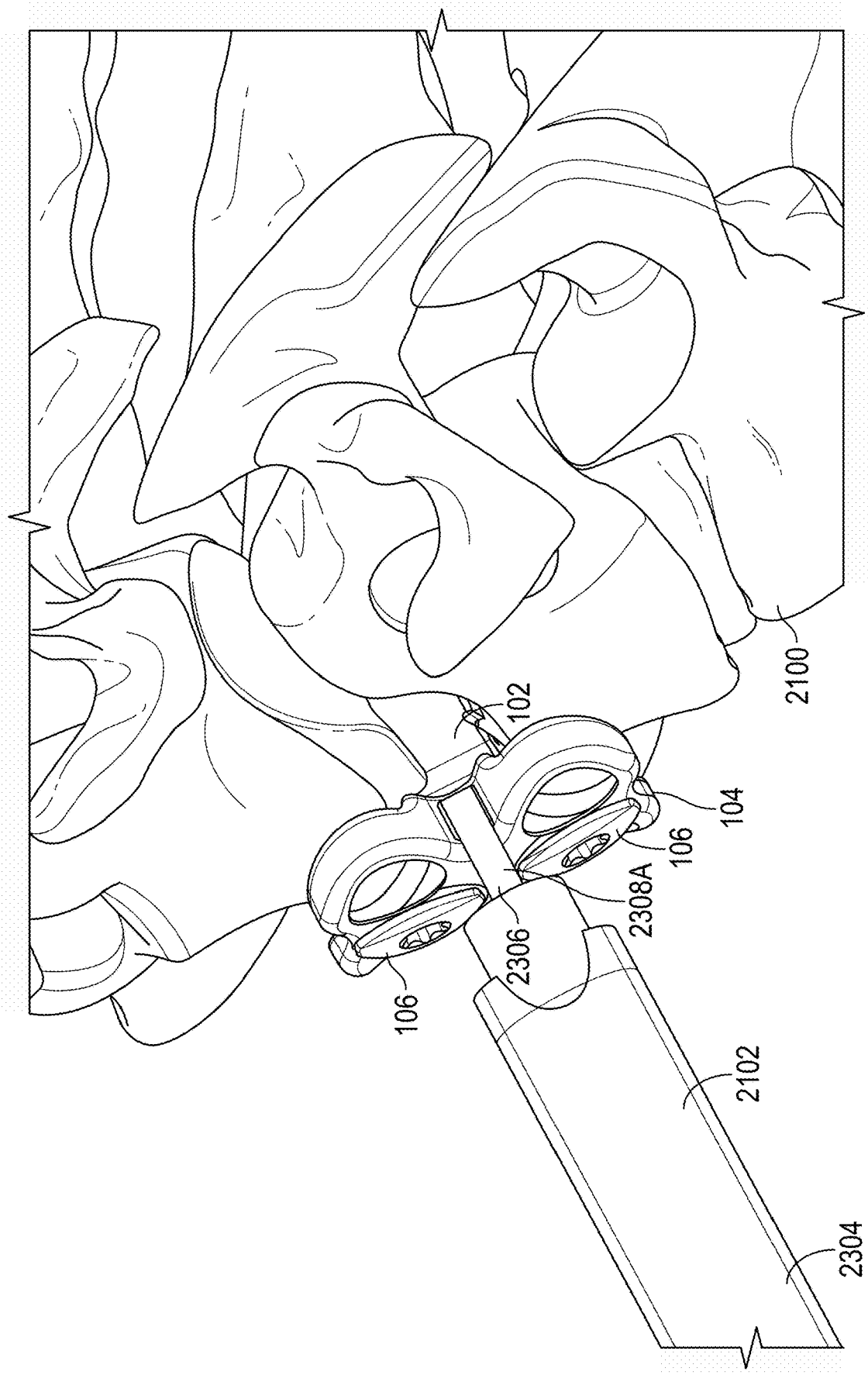
FIG. 22 illustrates another view of the spinal fixation system of FIG. 1 being implanted in a spine with the tool.

FIGS. 21 and 22 illustrate the spinal fixation system 100 being implanted into vertebrae 2100. As illustrated in FIGS. 21 and 22, an implanting tool 2102 may selectively engage the tool pockets 138 of the plate 104 during implantation to insert the spinal fixation system 100 into the vertebrae 2100.

FIGS. 23 and 24 illustrate the implanting tool 2102 in greater detail. As illustrated in FIGS. 23 and 24, the implanting tool 2102 generally includes a body 2304 and an engagement feature 2306. In the example of FIGS. 23 and 24, the engagement feature 2306 is a body with a pair of hooks 2308A-B. In some examples, the body 2304 is hollow, and the engagement feature 2306 is at least partially positioned within the body 2304. In various examples, the engagement feature 2306 is removable from the body 2304 such that another type of engagement feature may be used with the implanting tool 2102.

As best illustrated in FIG. 24, in some examples the implanting tool 2102 may include a knob 2309 or other suitable device that is engaged with the engagement feature 2306 to control at least one aspect of the engagement feature 2306. In the example of FIGS. 23 and 24, the knob 2309 is rotatably supported on the body 2304 and threadably engaged with the engagement feature 2306 to move the engagement feature 2306 in a linear direction (represented by arrow 2401) and thereby control how much of the engagement feature 2306 is retained within the body 1204. In the example of FIGS. 23 and 24, by controlling how much of the engagement feature 2306 is within the body 2304, and because the hooks 2308A-B have non-planar surfaces 2310, a distance 2403 between the hooks 2308A-B may be controlled and adjusted as desired (e.g., to be increased or decreased compared to that illustrated in FIG. 24).

Figure 25:
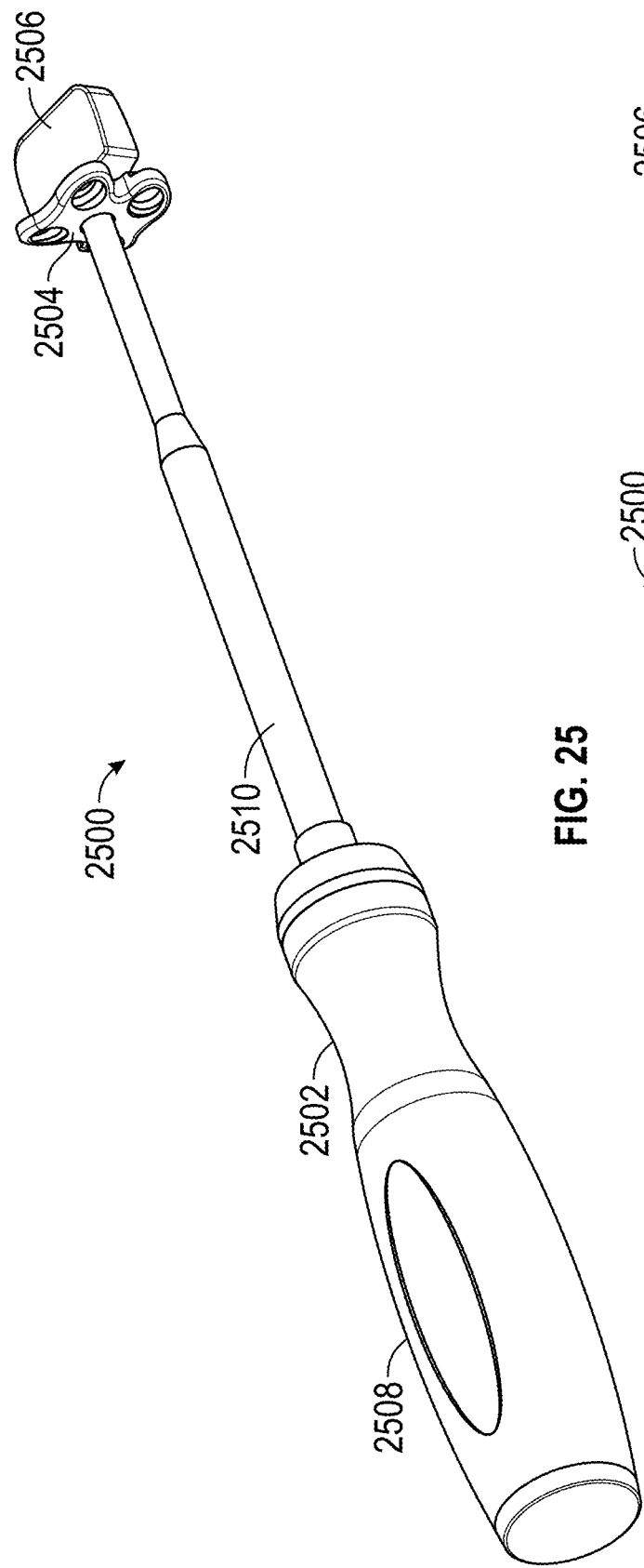
FIG. 25 is a perspective view of a trial system according to aspects of the current disclosure.
Figure 26:
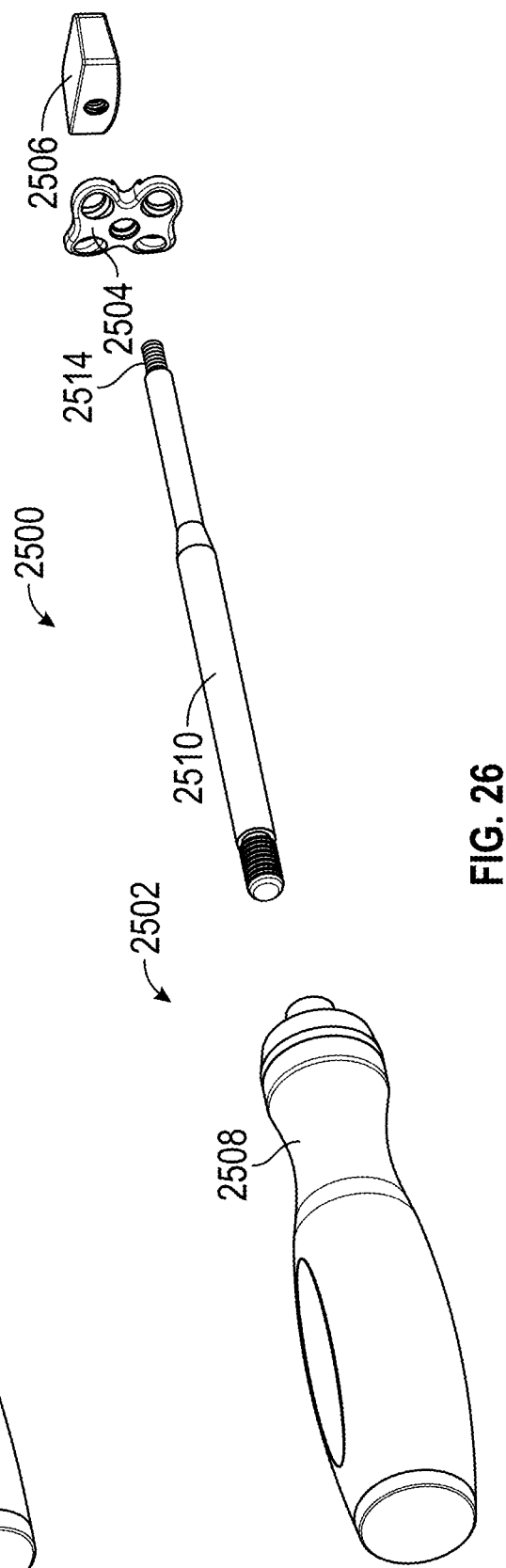
FIG. 26 is an exploded perspective view of the trial system of FIG. 25.
Figure 27:
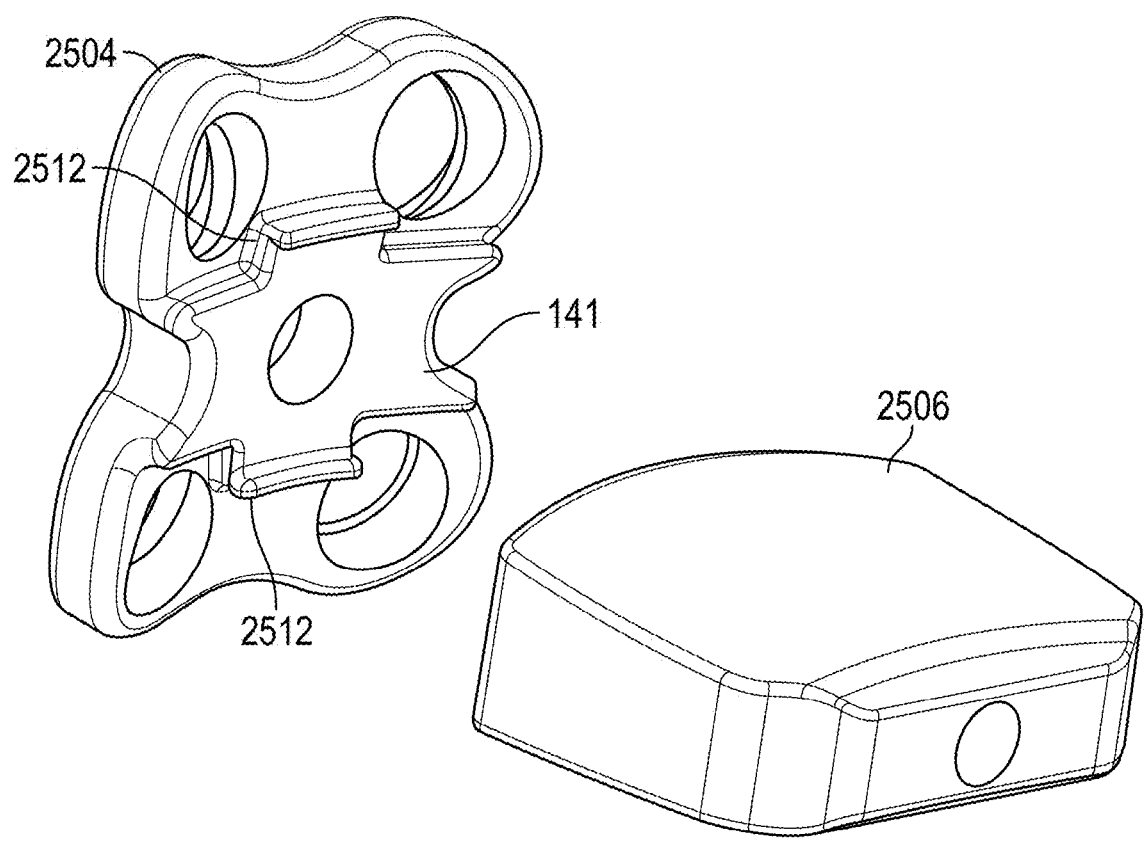
FIG. 27 is a perspective view of a trial plate and a trial body of the trial system of FIG. 25.

FIGS. 25-27 illustrate an example of a trial system 2500 according to aspects of the current disclosure. In some examples, and as explained in detail below, the trial system 2500 may be utilized to determine a correct size of a spinal fixation system for a patient before the final spinal fixation system is implanted.

As illustrated in FIGS. 25-27, the trial system 2500 generally includes a template tool 2502, a trial plate 2504, and a trial body 2506. The template tool 2502 includes a handle 2508 and an engaging portion 2510. In some examples, as illustrated in FIG. 26, the engaging portion 2510 is removably attached to the handle 2508 through various suitable mechanisms such as threading, hooks, pins, snaps, locks, etc. as desired. In other examples, the engaging portion 2510 and the handle 2508 are a single component.

The trial plate 2504 may generally have a shape and size that corresponds to a particular size of a plate of the spinal fixation system. Similarly, the trial body 2506 may have a shape and size that corresponds to a particular size of an interbody of the spinal fixation system. The trial plate 2504 may include alignment ribs 2512 that assist with positioning the trial plate 2504 relative to the trial body 2506. An end 2514 of the engaging portion 2510 may engage the trial plate 2504 and/or the trial body 2506 to give an approximation of the spinal fixation system and/or the inserter tool during implantation. In some cases, the end 2514 includes threading, and the trial plate 2504 and trial body 2506 include apertures configured to engage the end 2514 (with or without threading). In other examples, various other suitable engagement mechanisms may be utilized to engage the engaging portion 2510 with the trial plate 2504 and/or the trial body 2506.

In some cases, the trial system 2500 may be used to simulate an implantation procedure, and based on the simulation (or other measurements), a doctor or other professional may determine the appropriate sized spinal fixation system. For example, the doctor may determine that a larger or smaller plate 104 and/or interbody 102 during an actual implant procedure for a patient based on the trial system 2500. In other words, the trial system 2500 may be used to verify or determine what size implants need to be used.

Figure 28:
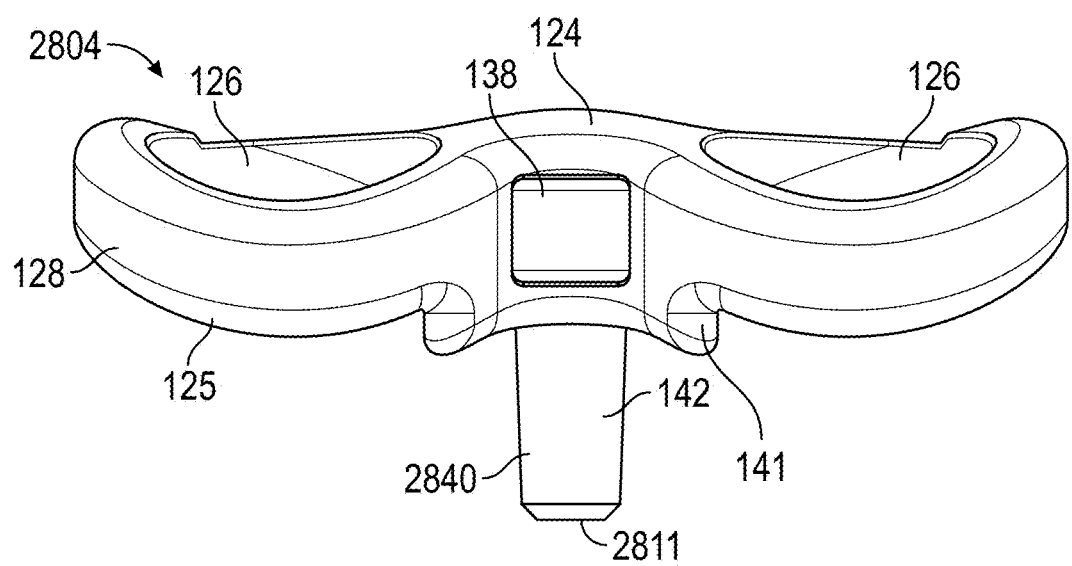
FIG. 28 is a side view of a plate of a spinal fixation system according to aspects of the current disclosure.

FIG. 28 illustrates another example of a plate 2804 for a spinal fixation system according to aspects of the current disclosure. The plate 2804 is substantially similar to the plate 104 except that locking projections 2840 of the plate 2804 (only one locking projection 2840 is visible in FIG. 28) do not include locking ribs 146 and the stem portion 142 does not include flex members 144. Instead, the locking projections 2840 of the plate 2804 are tapered as they extend away from the back surface 125, and an end 2811 of each locking projection 2840 has a width that is less than a width of a portion of each locking projection 2840 that is closer to the back surface 125. In certain embodiments, the tapered locking projections 2840 are configured to form a press fit or friction fit with an interbody of the spinal fixation system (e.g., the interbody 102) such that the interbody and plate 2804 are retained together.

Referring to FIGS. 1-8, a method of assembling the spinal fixation system 100 is also disclosed. In various aspects, the method includes assembling the plate 104 with the interbody 102 such that a position and orientation of the plate 104 relative to the interbody 102 is maintained. In some cases, assembling the plate 104 with the interbody 102 includes positioning the back surface 125 of the plate 104 adjacent to the front surface 110 of the interbody 102. Assembling the plate 104 with the interbody 102 also includes positioning the locking projections 140 of the plate 104 within the locking apertures 122 of the interbody 102. In certain cases, positioning the locking projections 140 within the corresponding locking apertures 122 includes inserting the stem portion 142 within the locking aperture 122 such that the locking ribs 146 engage the interbody 102 and the interbody 102 and the plate 104 are retained together. Assembling the plate 104 with the interbody 102 may also include positioning the locking collars 108 in the corresponding locking collar recesses 132. In some cases, each locking collar 108 is assembled by engaging the locking arms 158 and/or locking notches 160 with the alignment ribs 134 of the plate 104.

The method includes assembling the locking cams 106 with the assembled interbody 102 and the plate 104. In various aspects, assembling each locking cam 106 includes inserting the stem portion 152 into the corresponding locking cam aperture 130 and the collar 150 within the locking cam recess 136. Assembling each locking cam 106 may include engaging collar ribs 156 with corresponding cam-locking notches 162 of the locking collar 108.

The method may include implanting the assembled spinal fixation system 100 into vertebrae 2100 of the patient. Implanting the spinal fixation system 100 may include engaging an implanting tool 2102 with tool pockets 138 of the plate 104. Bone screws may be inserted through the bone screw apertures 126. Inserting the bone screws may include initially rotating the locking cam 106 such that the tab portion 148 is in the unlocked configuration. The bone screws are then inserted through the bone screw apertures 126 to engage the vertebrae 2100 of the patient and secure the spinal fixation system within the patient's body. After the bone screws are inserted and engaged with the vertebrae, the tab portion 148 may be rotated to the locked configuration.

In some examples, prior to assembling the spinal fixation system, the method may include determining a spinal fixation system size using the trial system 2500. Determining the size of the spinal fixation system may include assembling the trial system 2500 with the trial plate 2504 and the trial body 2506. The trial plate 2504 corresponds to a particular sized plate of the spinal fixation system, and the trial body 2506 corresponds to a particular sized interbody of the spinal fixation system. In some examples, the method includes simulating at least a portion of an implant procedure with the trial system 2500. In various examples, the method includes determining a proper size of the plate 104 and/or the interbody 102 based on and relative to the size of the trial plate 2504 and the trial body 2506. Based on the trial system 2500, a desired plate 104 and/or interbody 102 are provided to the doctor or professional. For example, the desired plate 104 and interbody 102 may be attached together, connected to an inserter tool (e.g., via engagement features 2306), and implanted into a disc space.

The spinal fixation system described herein has many advantageous features. For example, the spinal fixation system may be configured so that it directs the screw angle trajectory of the bone screws and at anterior corners of the patient's vertebrae to facilitate maximum purchase of the screws into the patient's cortical shell.

As another example, the design of the spinal fixation system maximizes the utilization of PEEK (or other biocompatible material) of the interbody while still providing titanium on titanium fixation. For example, the spinal fixation system with the titanium plate and bone screws and HA PEEK interbody reduces the amount of titanium in the spinal fixation system as compared to conventional spinal fixation systems. This is advantageous because PEEK more closely resembles cortical bone and is therefore more biomechanically acceptable. As a further example, because more biomechanically acceptable material is available for contact (through the increase in the PEEK material on the upper surface and lower surface), the interbody may promote surface area contact as compared to conventional spinal fixation systems. This in turn may promote an increase in fusion velocity as compared to conventional spinal fixation systems. This increased surface area also helps the interbody resist subsidence.

In addition, a reduced amount of titanium allows for better imaging of the spinal fixation system and the portion of the patient's body with the spinal fixation system. The spinal fixation system design also eliminates the need to snap the spinal fixation system into place and then insert a metal ring to retain it in position, which may otherwise introduce imaging issues.

Moreover, in some cases, the configuration of the spinal fixation system facilitates proper anterior-posterior placement of the spinal fixation system within a patient and/or increases torsional stability of the spinal fixation system. As yet another advantage, the spinal fixation system has superior attachment capabilities, which results in a stronger overall fixation of the spinal fixation system to the vertebrae.

In some cases, the design of the interbody is such that it can be used in isolation if needed (i.e., without the plate). This is possible because the plate can be omitted while allowing for a front surface with structural integrity. Moreover, the spinal fixation system is designed to facilitate ease of installation in that the plate can be snapped into place on the front surface of the interbody into the predefined configuration rather than requiring other alignment of the plate relative to the interbody.

A collection of exemplary examples, including at least some explicitly enumerated as "ECs" (Example Combinations), providing additional description of a variety of example types in accordance with the concepts described herein are provided below. These examples are not meant to be mutually exclusive, exhaustive, or restrictive; and the invention is not limited to these example examples but rather encompasses all possible modifications and variations within the scope of the issued claims and their equivalents.

EC 1. A spinal fixation system comprising: an interbody defining a locking aperture; and a plate comprising a front surface, a back surface, a locking projection extending from the back surface, and at least one bone screw aperture extending from the front surface to the back surface, wherein the locking projection is removably engaged with the locking aperture such that the plate is removably coupled to the interbody.

EC 2. The spinal fixation system of any of the preceding or subsequent example combinations, wherein the interbody comprises a front surface and a central opening, wherein the locking aperture extends from the front surface to the central opening, and wherein the locking projection is removably engaged with the locking aperture such that a locking rib of the locking projection engages the interbody within the central opening.

EC 3. The spinal fixation system of any of the preceding or subsequent example combinations, wherein the locking aperture is a first locking aperture, wherein the locking projection is a first locking projection, wherein the interbody further comprises a second locking aperture, and wherein the plate further comprises a second locking projection that is removably engaged with the second locking aperture.

EC 4. The spinal fixation system of any of the preceding or subsequent example combinations, wherein the plate further defines a locking cam aperture extending from the front surface to the back surface of the plate, wherein the spinal fixation system further comprises a locking cam comprising a tab and a stem, and wherein the stem of the locking cam is removably positioned within the locking cam aperture.

EC 5. The spinal fixation system of any of the preceding or subsequent example combinations, wherein the front surface of the plate comprises a locking collar recess surrounding the locking cam aperture, wherein the locking cam further comprises a collar, and wherein the collar of the locking cam is positioned within the locking collar recess.

EC 6. The spinal fixation system of any of the preceding or subsequent example combinations, further comprising a locking collar, wherein the locking collar is positioned within the locking collar recess and is configured to selectively engage the collar of the locking cam.

EC 7. The spinal fixation system of any of the preceding or subsequent example combinations, wherein the at least one bone screw aperture comprises a plurality of bone screw apertures.

EC 8. A spinal fixation system comprising: an interbody defining a locking aperture; a plate comprising a locking projection and defining a locking cam aperture; and a locking cam comprising a stem and a tab, wherein the locking projection is removably engaged with the locking aperture, and wherein the stem of the locking cam is at least partially positioned within the locking cam aperture.

EC 9. The spinal fixation system of any of the preceding or subsequent example combinations, wherein the plate further defines at least one bone screw aperture extending through the plate from a front surface of the plate to a back surface of the plate, wherein the locking projection extends outwardly from the back surface of the plate, and wherein the locking cam aperture extends from the front surface of the plate to the back surface of the plate.

EC 10. The spinal fixation system of any of the preceding or subsequent example combinations, wherein the interbody comprises a front surface and a central opening, wherein the locking aperture extends from the front surface to the central opening, and wherein the locking projection is removably engaged with the locking aperture such that a locking rib of the locking projection engages the interbody within the central opening.

EC 11. The spinal fixation system of any of the preceding or subsequent example combinations, wherein the locking projection comprises a stem, wherein the stem comprises a flex member, and wherein the flex member comprises a locking rib.

EC 12. The spinal fixation system of any of the preceding or subsequent example combinations, wherein a front surface of the plate comprises a locking collar recess surrounding the locking cam aperture, wherein the locking cam further comprises a collar, and wherein the collar of the locking cam is positioned within the locking collar recess.

EC 13. The spinal fixation system of any of the preceding or subsequent example combinations, further comprising a locking collar, wherein the locking collar is positioned within the locking collar recess and is configured to selectively engage the collar of the locking cam.

EC 14. The spinal fixation system of any of the preceding or subsequent example combinations, wherein the front surface of the plate further comprises a locking cam recess at least partially surrounding the locking collar recess, and wherein tab of the locking cam is movable within the locking cam recess.

EC 15. A plate for a spinal fixation system, the plate comprising: a body comprising a front surface and a back surface; a locking projection extending outwardly from the back surface of the body; a locking cam aperture extending through the body from the front surface to the back surface; and a bone screw aperture extending through the body from the front surface to the back surface.

EC 16. The plate of any of the preceding or subsequent example combinations, wherein the body further comprises a perimeter surface between the front surface and the back surface, and wherein the perimeter surface defines at least one tool pocket.

EC 17. The plate of any of the preceding or subsequent example combinations, further comprising a locking collar recess in the front surface of the body and surrounding the locking cam aperture.

EC 18. The plate of any of the preceding or subsequent example combinations, wherein the locking collar recess further comprises at least one locking rib.

EC 19. The plate of any of the preceding or subsequent example combinations, further comprising a locking cam recess in the front surface of the body at least partially surrounding the locking collar recess.

EC 20. The plate of any of the preceding or subsequent example combinations, wherein the locking projection is a first locking projection, and wherein the plate further comprises a plurality of locking projections extending outwardly from the back surface.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed:

1. A spinal fixation system comprising:
    an interbody comprising a front surface, a back surface, a top end, a bottom end, a central opening, a first locking aperture defined in the front surface between the top end and the bottom end and extending from the front surface to the central opening, and a second locking aperture defined in the front surface between the top end and the bottom end and extending from the front surface to the central opening; and
    a plate comprising a front surface, a back surface, a first locking projection, a second locking projection, at least one upper bone screw aperture extending from the front surface to the back surface, at least one lower bone screw aperture extending from the front surface to the back surface of the plate, a ridge extending outwards from the back surface between the at least one upper bone screw aperture and the at least one lower bone screw aperture, wherein the first locking projection and the second locking projection are each on the ridge and extend outwards from the ridge, wherein, in an assembled configuration of the plate with the interbody, the first locking projection is removably engaged with the first locking aperture of the interbody such that the first locking projection engages the interbody within the central opening and the second locking projection is removably engaged with the second locking aperture such that the second locking projection engages the interbody within the central opening such that the plate is removably coupled to the interbody, wherein the first locking projection and the second locking projection are each unthreaded, and wherein the first locking projection and the second locking projection each comprise:
    a stem portion and a head portion, the head portion comprising a plurality of flex members and a plurality of locking ribs opposite from the back surface of the plate,
    wherein adjacent flex members are separated by a notch,
    wherein the plurality of ribs are on the plurality of flex members,
    wherein the plurality of ribs define a maximum width of the head portion,
    wherein the plurality of flex members are flexible relative the stem portion such that the head portion is adjustable between a compressed configuration and an uncompressed configuration,
    wherein, in the uncompressed configuration, the maximum width of the head portion is greater than a width of the first locking aperture and greater than a width of the second locking aperture, and
    wherein, in the assembled configuration, the head portion is in the uncompressed configuration and the plurality of ribs overlap a portion of the interbody such that the portion of the interbody is retained between the plurality of ribs and the back surface of the plate.

2. The spinal fixation system of claim 1, wherein the plate further defines a locking cam aperture extending from the front surface to the back surface of the plate, wherein the spinal fixation system further comprises a locking cam comprising a tab and a stem, and wherein the stem of the locking cam is removably positioned within the locking cam aperture.

3. The spinal fixation system of claim 2, wherein the front surface of the plate comprises a locking collar recess surrounding the locking cam aperture, wherein the locking cam further comprises a collar, and wherein the collar of the locking cam is positioned within the locking collar recess.

4. The spinal fixation system of claim 3, further comprising a locking collar, wherein the locking collar is positioned within the locking collar recess and is configured to selectively engage the collar of the locking cam.

5. The spinal fixation system of claim 1, wherein the first locking projection and the second locking projection are each integrally formed with the plate.

6. A spinal fixation system comprising:
    an interbody comprising a front surface, a top end, a bottom end, a central opening, a first locking aperture defined in the front surface between the top end and the bottom end and extending from the front surface to the central opening, and a second locking aperture defined in the front surface between the top end and the bottom end and extending from the front surface to the central opening, wherein the first locking aperture and the second locking aperture each comprises a central axis, and wherein the central axis of the first locking aperture is parallel with the central axis of the second locking aperture;
    a plate comprising a first locking projection, a second locking projection, at least one upper bone screw aperture extending from a front surface to a back surface of the plate, at least one lower bone screw aperture extending from the front surface to the back surface of the plate, a ridge extending outwards from the back surface between the at least one upper bone screw aperture and the at least one lower bone screw aperture, and a locking cam aperture defined in the plate, wherein the first locking projection and the second locking projection are each on the ridge and extend outwards from the ridge, wherein the first locking projection and the second locking projection are each unthreaded; and a locking cam comprising a stem and a tab, wherein the first locking projection is positionable within the first locking aperture such that the first locking projection is removably engaged with the first locking aperture by overlapping a portion of the interbody defining the first locking aperture and extending into the central opening, wherein the second locking projection is positionable within the second locking aperture such that the second locking projection is removably engaged with the second locking aperture by overlapping a portion of the interbody defining the second locking aperture and extending into the central opening, and wherein the stem of the locking cam is at least partially positioned within the locking cam aperture.

7. The spinal fixation system of claim 6, wherein the locking cam aperture extends from the front surface of the plate to the back surface of the plate.

8. The spinal fixation system of claim 6, wherein each of the first locking projection and the second locking projection comprises ribs for engaging the interbody within the central opening.

9. The spinal fixation system of claim 6, wherein the first locking projection comprises a stem, wherein the stem comprises a flex member, wherein the flex member comprises a locking rib, and wherein the first locking projection and the plate are integrally formed.

10. The spinal fixation system of claim 6, wherein a front surface of the plate comprises a locking collar recess surrounding the locking cam aperture, wherein the locking cam further comprises a collar, and wherein the collar of the locking cam is positioned within the locking collar recess.

11. The spinal fixation system of claim 10, further comprising a locking collar, wherein the locking collar is positioned within the locking collar recess and is configured to selectively engage the collar of the locking cam.

12. The spinal fixation system of claim 10, wherein the front surface of the plate further comprises a locking cam recess at least partially surrounding the locking collar recess, and wherein the tab of the locking cam is movable within the locking cam recess.

13. A plate for a spinal fixation system, the plate comprising:
a body comprising a front surface, a back surface, and a perimeter surface between the front surface and the back surface, wherein the perimeter surface defines at least one tool pocket between the front surface and the back surface, the at least one tool pocket comprising a bottom pocket surface that is recessed into the body of the plate relative to the perimeter surface and a side pocket surface extending from the perimeter surface to the bottom pocket surface;

a first locking projection and a second locking projection, the first locking projection and the second locking projection each extending outwardly from the back surface of the body, wherein each of the first locking projection and the second locking projection are unthreaded and configured to engage an interbody of the spinal fixation system, wherein the first locking projection extends parallel to the second locking projection, and wherein the first locking projection and the second locking projection each comprise:
a stem portion and a head portion, the head portion comprising one or more flex members and one or more locking ribs opposite from the back surface of the plate,
wherein the one or more locking ribs are on the one or more flex members,
wherein the one or more ribs define a maximum width of the head portion,
wherein the one or more flex members are flexible relative the stem portion such that the head portion is adjustable between a compressed configuration and an uncompressed configuration;

a locking cam aperture extending through the body from the front surface to the back surface, wherein the locking cam aperture is vertically offset from the locking projection such that the locking cam aperture is configured to extend above or below the interbody;

a bone screw aperture extending through the body from the front surface to the back surface; and a ridge extending outwards from the back surface, wherein the first locking projection and the second locking projection are each on the ridge and extend outwards from the ridge.

14. The plate of claim 13, further comprising a locking collar recess in the front surface of the body and surrounding the locking cam aperture.

15. The plate of claim 14, wherein the locking collar recess further comprises at least one locking rib.

16. The plate of claim 14, further comprising a locking cam recess in the front surface of the body at least partially surrounding the locking collar recess.

* * * * *